United States Patent

Tomioka et al.

Patent Number: 5,563,174
Date of Patent: Oct. 8, 1996

[54] HYDRAZONE COMPOUND AND INSECTICIDE CONTAINING SAID COMPOUND AS ACTIVE INGREDIENT

[75] Inventors: Hiroki Tomioka, Ikeda; Taro Hirose, Takatsuki; Toshiaki Taki, Toyonaka; Hirosi Kisida, Takarazuka; Shigeru Saito, Toyonaka, all of Japan

[73] Assignee: Sumitomo Chemical Company, Limited, Osaka-fu, Japan

[21] Appl. No.: 370,861

[22] Filed: Jan. 10, 1995

[30] Foreign Application Priority Data

Jan. 24, 1994 [JP] Japan ..................... 6-006012
Jan. 24, 1994 [JP] Japan ..................... 6-006016
May 26, 1994 [JP] Japan ..................... 6-112979

[51] Int. Cl.$^6$ ................ A01N 41/04; C07C 309/29
[52] U.S. Cl. .............. 514/517; 514/519; 558/53; 558/54; 558/56; 558/58
[58] Field of Search ................ 564/251, 250; 514/639, 523, 519, 520, 517; 558/58, 53, 54, 426, 56

[56] References Cited

U.S. PATENT DOCUMENTS

| | | | |
|---|---|---|---|
| 4,344,893 | 8/1982 | Copping et al. | 558/53 |
| 4,394,387 | 7/1983 | Copping et al. | 514/517 |
| 5,340,837 | 8/1994 | Hall et al. | 514/603 |

*Primary Examiner*—Shailendra Kumar
*Attorney, Agent, or Firm*—Birch, Stewart, Kolasch & Birch, LLP

[57] ABSTRACT

A hydrazone compound of the general formula (I):

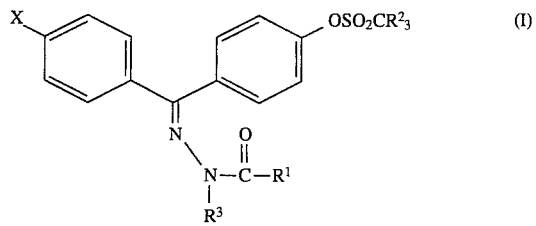

wherein X is halogen; $R^1$ is hydrogen, optionally substituted $C_1$–$C_4$ alkyl or optionally substituted $C_1$–$C_4$ alkoxy; $R^2$'s are independently hydrogen or fluorine; $R^3$ is a group of the general formula: $CH_2R^4$ wherein $R^4$ is cyano or $C_1$–$C_4$ alkoxy; or $R^3$ is a group of the general formula: $SR^5$ wherein $R^5$ is optionally substituted $C_1$–$C_{16}$ alkyl; optionally substituted phenyl, or the like, has excellent insecticidal activity and rather low toxicity to mammals. The hydrazone compound is useful as an active ingredient of insecticides for controlling harmful insects.

13 Claims, No Drawings

1

HYDRAZONE COMPOUND AND INSECTICIDE CONTAINING SAID COMPOUND AS ACTIVE INGREDIENT

FIELD OF THE INVENTION

The present invention relates to a hydrazone compound and an insecticide containing the compound as an active ingredient.

BACKGROUND OF THE INVENTION

It is well known that certain kinds of hydrazone compounds can be used as an active ingredient of insecticides (see, e.g., U.S. Pat. No. 4,344,893); they are, however, not satisfactory because of their acute toxicity to mammals.

SUMMARY OF THE INVENTION

Under these circumstances, the present inventors have intensively studied to find a compound having excellent insecticidal activity and low toxicity to mammals. As a result, they have found that particular kinds of hydrazone compounds comply with these requirements, thereby completing the present invention.

Thus, the present invention provides a hydrazone compound of the general formula (I):

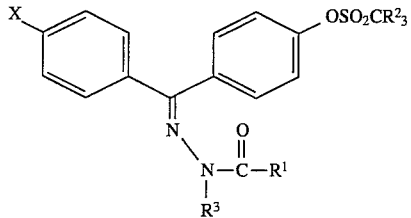

(I)

wherein X is halogen;

$R^1$ is hydrogen; $C_1$–$C_4$ alkyl which may be optionally substituted with halogen, cyano or $C_1$–$C_4$ alkoxy; or $C_1$–$C_4$ alkoxy which may be optionally substituted with halogen;

$R^2$'s are the same or different and are independently hydrogen or fluorine;

$R^3$ is a group of the general formula (II):

 (II)

wherein $R^4$ is cyano or $C_1$–$C_4$ alkoxy;

or $R^3$ is a group of the general formula (III):

 (III)

wherein $R^5$ is $C_1$–$C_{16}$ alkyl which may be optionally substituted with halogen; phenyl which may be optionally substituted with halogen, nitro or $C_1$–$C_{10}$ alkyl which may be optionally substituted with halogen; a group of the general formula (IV):

 (IV)

wherein $R^6$ and $R^7$ are the same or different and are independently $C_1$–$C_{16}$ alkyl which may be optionally substituted with halogen, cyano or $C_1$–$C_{16}$ alkoxy; $C_3$–$C_{16}$ alkenyl which may be optionally substituted with halogen; $C_3$–$C_{16}$ alkynyl which may be optionally substituted with halogen; phenyl which may be optionally substituted with halogen or $C_1$–$C_{10}$ alkyl which may be optionally substituted with halogen; $C_7$–$C_{16}$ phenylalkyl which may be optionally substituted with halogen or $C_1$–$C_{10}$ alkyl which may be optionally be substituted with halogen; $C_2$–$C_{16}$ alkoxycarbonyl; $C_3$–$C_{16}$ alkoxycarbonylalkyl; or $R^6$ and $R^7$ are combined together at their ends to form $C_4$–$C_7$ alkylene which may be optionally substituted with $C_1$–$C_4$ alkyl or may optionally contain oxygen or sulfur; or $C_4$–$C_7$ alkenylene which may be optionally substituted with $C_1$–$C_4$ alkyl or may optionally contain oxygen or sulfur;

or $R^5$ is a group of the general formula (V):

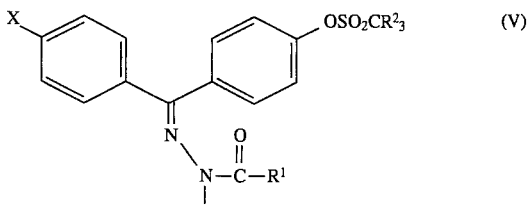 (V)

wherein X, $R^1$ and $R^2$ are each as defined above.

The present invention also provides an insecticide comprising the above hydrazone compound as an active ingredient, and a method for controlling harmful insects by use of the above hydrazone compound.

DETAILED DESCRIPTION OF THE INVENTION

The hydrazone compounds of the present invention are represented by the general formula (I) wherein the substituents X, $R^1$, $R^2$'s and $R^3$ are defined as follows:

The substituent X is halogen such as fluorine, chlorine, bromine or iodine.

The substituent $R^1$ is hydrogen; $C_1$–$C_4$ alkyl which may be optionally substituted with halogen, cyano or $C_1$–$C_4$ alkoxy; or $C_1$–$C_4$ alkoxy which may be optionally substituted with halogen.

Examples of the $C_1$–$C_4$ alkyl which may be optionally substituted with halogen, cyano or $C_1$–$C_4$ alkoxy are methyl, ethyl, propyl, isopropyl, butyl, isobutyl, sec-butyl, tert-butyl, difluoromethyl, trifluoromethyl, 2,2,2-trifluoroethyl, 1,1,2,2-tetrafluoroethyl, pentafluoroethyl, chloromethyl, bromomethyl, 2-chloroethyl, 4-chlorobutyl, cyanomethyl, 2-cyanoethyl, 2-cyanopropyl, 3-cyanopropyl, 4-cyanobutyl, methoxymethyl, ethoxymethyl, propoxymethyl, isopropoxymethyl, butoxymethyl, 1-methoxyethyl, 2-methoxyethyl, 1-ethoxyethyl, 2-ethoxyethyl, 2-propoxyethyl, 2-methoxypropyl, 3-methoxypropyl, 4-methoxybutyl, 4-butoxybutyl, 1-methyl-1-methoxyethyl, 2-methyl-2-methoxypropyl, 2-methyl-3-methoxypropyl, 2-methoxybutyl and 3-methoxybutyl.

Examples of the $C_1$–$C_4$ alkoxy which may be optionally substituted with halogen are methoxy, ethoxy, propoxy, isopropoxy, butoxy, sec-butoxy, 2-chloroethoxy, 2-fluoroethoxy, 1-chloro-2-methylpropoxy and 4-chlorobutoxy.

The substituents $R^2$'s are the same or different and are independently hydrogen or fluorine.

The substituent $R^3$ is a group of the general formula (II) or a group of the general formula (III).

The substituent $R^4$ is cyano or $C_1$–$C_4$ alkoxy such as methoxy, ethoxy, propoxy, isopropoxy or butoxy.

The substituent $R^5$ is $C_1$–$C_{16}$ alkyl which may be optionally substituted with halogen; phenyl which may be optionally substituted with halogen, nitro or $C_1$–$C_{10}$ alkyl which may be optionally substituted with halogen; a group of the general formula (IV); or a group of the general formula (V).

Examples of the $C_1$–$C_{16}$ alkyl which may be optionally substituted with halogen are methyl, ethyl, propyl, isopropyl, butyl, pentyl, undecyl, hexadecyl, chloromethyl, trichloromethyl, difluorochlorometyl, 6-chlorohexyl and 16-fluorohexadecyl.

Examples of the phenyl which may be optionally substituted with halogen, nitro or $C_1$–$C_{10}$ may be optionally substituted with halogen are phenyl, 4-fluorophenyl, 4-chlorophenyl, 4-bromophenyl, 2,4-dichlorophenyl, 4-methylphenyl, 4-ethylphenyl, 4-hexylphenyl, 4-decylphenyl, 4-trifluoromethylphenyl, 2-nitrophenyl, 4-nitrophenyl, 2,4-dinitrophenyl and 4-chloro-2-nitrophenyl.

The substituents $R^6$ and $R^7$ are the same or different and are independently $C_1$–$C_{16}$ alkyl which may be optionally substituted with halogen, cyano or $C_1$–$C_{16}$ alkoxy; $C_3$–$C_{16}$ alkenyl which may be optionally substituted with halogen; $C_3$–$C_{16}$ alkynyl which may be optionally substituted with halogen; phenyl which may be optionally substituted with halogen or $C_1$–$C_{10}$ alkyl which may be optionally substituted with halogen; $C_7$–$C_{16}$ phenylalkyl which may be optionally substituted with halogen or $C_1$–$C_{10}$ alkyl which may be optionally be substituted with halogen; $C_2$–$C_{16}$ alkoxycarbonyl; $C_3$–$C_{16}$ alkoxy-carbonylalkyl; or the substituents $R^6$ and $R^7$ are combined together at their ends to form $C_4$–$C_7$ alkylene which may be optionally substituted with $C_{1-C4}$ alkyl or may optionally contain oxygen or sulfur (e.g., tetramethylene, pentamethylene, —CH$_2$CH$_2$OCH$_2$CH$_2$—, —CH$_2$CH$_2$SCH$_2$CH$_2$—); or $C_4$–$C_7$ alkenylene which may be optionally substituted with $C_1$–$C_4$ alkyl or may optionally contain oxygen or sulfur (e.g., —CH$_2$CH=CHCH$_2$—, —CH=CHCH$_2$CH$_2$—, —CH$_2$CH=CHCH$_2$CH$_2$—).

Examples of the $C_1$–$C_{16}$ alkyl which may be substituted with halogen, cyano or $C_1$–$C_{16}$ alkoxy are methyl, ethyl, propyl, isopropyl, butyl, isobutyl, sec-butyl, hexyl, octyl, undecyl, hexadecyl, chloromethyl, chloroethyl, 5-chloropentyl, 10-chlorodecyl, 15-chloropentadecyl, 10fluorodecyl, cyanomethyl, 2-cyanoethyl, 5-cyanopentyl, 10-cyanodecyl, 15cyanopentadecyl, methoxymethyl, 2-methoxyethyl, 3-methoxypropyl, 10-methoxydecyl, 15-methoxypentadecyl, 3-(hexyloxy)propyl, 3-(undecyloxy)propyl and 3-(hexadecyloxy)propyl.

Examples of the $C_3$–$C_{16}$ alkenyl which may be substituted with halogen are 2-propenyl, 2-butenyl, 2-tetradecenyl, 2-hexadecenyl, 3-chloropropenyl, 3,3-dichloro-2-propenyl, 9-chloro-2-nonenyl and 16-chloro-2-hexadecenyl.

Examples of the $C_3$–$C_{16}$ alkynyl which may be substituted with halogen are 2-propynyl, 2-butynyl, 2-nonynyl, 2-hexadecynyl, 3-iodo-2-propynyl, 8-chloro-2-octynyl and 16-chloro-2-hexadecynyl.

Examples of the phenyl which may be substituted with halogen or $C_1$–$C_{10}$ alkyl which may be substituted with halogen am phenyl, 4-fluorophenyl, 4-chlorophenyl, 2,4-dichlorophenyl, 3,5-dichlorophenyl, 4-methylphenyl, 4-pentylphenyl, 4-decylphenyl, 4-trifluoromethylphenyl, 4-(5-chloropentyl)phenyl and 4-(10-chlorodecyl)-phenyl.

Examples of the $C_7$–$C_{16}$ phenylalkyl which may be optionally substituted with halogen or $C_1$–$C_{10}$ alkyl which may be optionally substituted with halogen are benzyl, 4-chlorobenzyl, β-phenetyl, 3phenylpropyl, 4-ethylbenzyl, 2(4-decylphenyl)-ethyl, 2-(4-chlorophenyl)ethyl, 4-(trifluoromethyl)benzyl and 2-(4-(trifluoromethyl)phenyl)-ethyl.

Examples of the $C_2$–$C_{16}$ alkoxycarbonyl are methoxycarbonyl, ethoxycarbonyl, propoxycarbonyl, isopropoxycarbonyl, butoxycarbonyl, decyloxycarbonyl and pentadecyloxycarbonyl.

Examples of the $C_3$–$C_{16}$ alkoxycarbonylalkyl are methoxycarbonylmethyl, ethoxycarbonylmethyl, propoxycarbonyhnethyl, butoxycarbonylmethyl, hexyloxycarbonylmethyl, 2-(methoxycarbonyl)ethyl, 2-(ethoxycarbonyl)ethyl, 2-(propoxycarbonyl)ethyl, 2-(isopropoxycarbonyl)ethyl, 2-(butoxycarbonyl)ethyl, 2-(hexyloxyocarbonyl)ethyl, 2-(octyloxycarbonyl)ethyl, 2-(dodecyloxycarbonyl)ethyl, 2-(tridecyloxycarbonyl)ethyl and 3-(methoxycarbonyl)propyl.

Among the preferred hydrazone compounds of the general formula (I) are those wherein X is chlorine; $R^1$ is $C_1$–$C_4$ alkyl or $C_{1-C4}$ alkoxy; $R^2$'s are all fluorine; and $R^3$ is a group of the general formula (II) wherein $R^4$ is cyano, methoxy or ethoxy; or $R^3$ is a group of the general formula (III) wherein $R^5$ is trichloromethyl or a group of the general formula (IV) wherein $R^6$ and $R^7$ are the same or different and are independently $C_1$–$C_4$ alkyl; benzyl which may be optionally substituted with halogen or $C_1$–$C_4$ alkyl which may be optionally substituted with halogen; $C_2$–$C_3$ alkoxycarbonyl; or $C_3$–$C_5$ alkoxycarbonylalkyl. More preferably, $R^1$ is $C_1$–$C_4$ alkoxy, R 4 is cyano, and $R^5$ is a group of the general formula (IV) wherein $R^6$ and $R^7$ are the same or different and are independently $C_1$–$C_4$ alkyl, benzyl, $C_2$–$C_3$ alkoxycarbonyl or $C_3$–$C_5$ alkoxycarbonylalkyl. Most preferably, $R^1$ is methoxy or ethoxy.

The hydrazone compounds of the present invention can be produced, for example, by the following production process (A).

Production Process (A)

The process comprises reacting a compound of the general formula (VI):

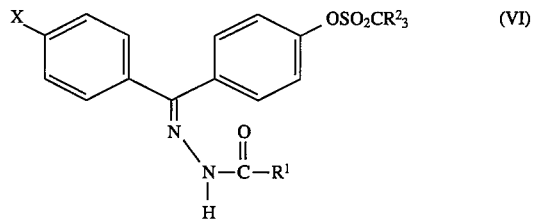

(VI)

wherein X is halogen; $R^1$ is hydrogen; $C_1$–$C_4$ alkyl which may be optionally substituted with halogen, cyano or $C_1$–$C_4$ alkoxy; or $C_1$–$C_4$ alkoxy which may be optionally substituted with halogen; and $R^2$'s are the same or different and are independently hydrogen or fluorine with a compound of the general formula (VII):

$Y$-$CH_2$-$R^4$ (VII)

wherein Y is halogen (e.g., chlorine, bromine) and $R^4$ is cyano or $C_1$–$C_4$ alkoxy, or with a compound of the general formula (VIII):

$Y$-$S$-$R^5$ (VIII)

wherein Y is halogen (e.g., chlorine, bromine) and $R^5$ is $C_1$–$C_{16}$ alkyl which may be optionally sustituted with halogen; phenyl which may be optionally substituted with halogen, nitro or $C_1$–$C_{10}$ alkyl which may be optionally substituted with halogen; a group of the general formula (IV); or a group of the general formula (V).

The reaction is usually effected in the presence of a base. Examples of the base which can be used are organic bases such as triethylamine, pyridine, 4-N,N-dimethylaminopyridine and N,N-diethylanniline; inorganic bases such as sodium hydroxide, sodium hydride and potassium carbonate; and organic metal bases such as n-butyl lithium and lithium diisopropylamine.

In the production process (A), it is not necessary to use a solvent; the reaction is, however, effected in an inert solvent. When a solvent is used, it depends upon the kind of base used. Typical examples of the solvent are aromatic hydrocarbons such as benzene, toluene and xylene; pyridine compounds such as pyridine and picoline; halogenated hydrocarbons such as chloroform, carbon tetrachloride, 1,2-dichloroethane, 1,1,1-trichloroethane, tetrachloroethylene, trichloroethylene, chlorobenzene and o-dichlorobenzene; aliphatic hydrocarbons such as n-hexane and n-heptane; alicyclic hydrocarbons such as cyclohexane; aprotic polar solvents such as N,N-dimethylformamide and dimethylsulfoxide; ethers such as tetrahydrofuran and diethylether; ketones such as acetone and methyl isobutyl ketone; or mixtures thereof.

The amounts of reaction reagents to be used in the production process (A) are usually in the range of 1 to 100 moles per mole of the compound of the general formula (VI) for each of the base and the compound of the general formula (VII) or (VIII). The reaction temperature is usually in the range of −78° C. to 200° C.

After completion of the reaction, ordinary post-treatments such as organic solvent extraction and concentration are conducted to isolate the desired compound of the present invention; if necessary, purification may be conducted by a technique such as chromatography or recrystallization.

The compound (VI) which is used as the starting material in the production process (A) can be produced, for example, by the following production process (a).

Production Process (a)

The process comprises reacting a compound of the general formula (IX):

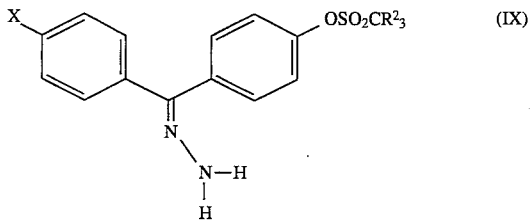

(IX)

wherein X and $R^2$ are each as defined above, with a compound of the general formula (X):

(X)

wherein $R^1$ is as defined above and W is chlorine, bromine or $-OCOR^1$.

In this process, the reaction is usually effected in the presence of a base. Examples of the base which can be used are organic bases such as triethylamine, pyridine, 4-N,N-dimethylaminopyridine and N,N-diethylaniline; inorganic bases such as sodium hydroxide, sodium hydride and potassium carbonate; organic metal bases such as n-butyl lithium and lithium diisopropylamine.

In this process, it is not necessary to use a solvent; it is, however, generally preferred that the reaction is effected in an inert solvent. When a solvent is used, it depends upon the substituent W in the general formula (X) or the kind of base used. Typical examples of the solvent are aromatic hydrocarbons such as benzene, toluene and xylene; pyridine compounds such as pyridine and picoline; halogenated hydrocarbons such as chloroform, carbon tetrachloride, 1,2-dichloroethane, 1,1,1-trichloroethane, tetrachloroethylene, trichloroethylene, chlorobenzene: and o-dichlorobenzene; aliphatic hydrocarbons such as n-hexane and n-heptane; alicyclic hydrocarbons such as cyclohexane; alcohols such as methanol, ethanol and isopropanol; aprotic polar solvents such as N,N-dimethylfonnamide and dimethylsulfoxide; ethers such as tetrahydrofuran and diethyl-ether; ketones such as acetone and methyl isobutyl ketone; water; or mixtures thereof.

The amounts of reaction reagents to be used in the production process (a) are usually in the range of 1 to 100 moles per mole of the compound of the general formula (IX) for each of the base and the compound of the general formula (X). The reaction temperature is usually in the range of −20° C. to 200° C.

After completion of the reaction, ordinary post-treatments such as extraction with an organic solvent and concentration are conducted to isolate the compound of the general formula (VI).

The compound of the general formula (IX) which is used as the starting material in the production process (a) is a known compound, which can be produced, for example, by a process as described in the U.S. Pat. No. 4,344,893.

The hydrazone compound of the present invention may have two kinds of geometrical isomers (i.e., E- mid Z-isomers), based on the configuration of a C=N double bond in the hydrazine moiety, and it should be recognized that these geometrical isomers and mixtures thereof are included within the scope of the present invention.

Examples of the hydrazone compound of the present invention are shown in Tables 1 to 3.

TABLE 1

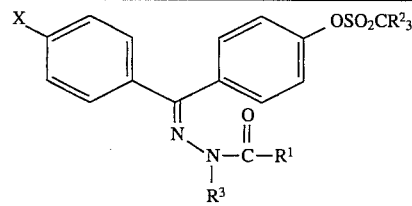

wherein $R^2$ is fluorine, $R^3$ is $CH_2R^4$, and X, $R^1$ and $R^4$ are each as defined below.

| X | $R^1$ | $R^4$ |
|---|---|---|
| Cl | $CH_3$ | $OCH_2CH_3$ |
| Cl | $CH_3$ | $OCH_3$ |
| Cl | $CH_3$ | $OCH(CH_3)_2$ |
| Cl | $OCH_2CH_3$ | $OCH_2CH_3$ |
| Cl | $OCH_2CH_3$ | $OCH(CH_3)_2$ |
| Cl | $CH_2CH_2CH_3$ | $OCH_2CH_3$ |
| Cl | $CH_2CH_3$ | $OCH_3$ |
| Cl | $CH_2CH_2CH_3$ | $OCH_3$ |
| Cl | $CH_2OCH_3$ | $OCH_3$ |
| Cl | $CH_3$ | $OCH_2CH_2CH_3$ |
| Cl | $OCH_2CH_3$ | $OCH_3$ |
| Cl | $OCH_2CH_3$ | $OCH_2CH_2CH_3$ |
| Cl | $CH_2CH_2CH_2CH_3$ | $OCH_2CH_3$ |
| Cl | $CH_2CH_3$ | $OCH_2CH_3$ |
| Cl | $CH_2CH_3$ | $OCH(CH_3)_2$ |
| Cl | $CH_2CH_2CH_2CH_3$ | $OCH_3$ |
| Cl | $CH_2CH_2CH_2CH_3$ | $OCH_2CH_3$ |
| Cl | $CH_2CH_2CH_2CH_3$ | $OCH(CH_3)_2$ |
| Cl | $CH_2CH_2CH_2CH_3$ | $OCH_2CH_2CH_3$ |
| Cl | $CH(CH_3)_2$ | $OCH_3$ |
| Cl | $CH(CH_3)_2$ | $OCH_2CH_3$ |
| Cl | $CH(CH_3)_2$ | $OCH(CH_3)_2$ |
| Cl | $CH(CH_3)_2$ | $OCH_2CH_2CH_3$ |
| Cl | $CH_2CH(CH_3)_2$ | $OCH_3$ |
| Cl | $CH_2CH(CH_3)_2$ | $OCH_2CH_3$ |

TABLE 1-continued

[Structure: X-C6H4-C(=N-N(R3)-C(=O)-R1)-C6H4-OSO2CR2_3]

wherein $R^2$ is fluorine, $R^3$ is $CH_2R^4$,
and X, $R^1$ and $R^4$ are each as defined below.

| X | $R^1$ | $R^4$ |
|---|---|---|
| Cl | $CH_2CH(CH_3)_2$ | $OCH(CH_3)_2$ |
| Cl | $CH_2CH(CH_3)_2$ | $OCH_2CH_2CH_3$ |
| Cl | $OCH_3$ | $OCH_3$ |
| Cl | $OCH_3$ | $OCH_2CH_3$ |
| Cl | $OCH_3$ | $OCH_2CH_2CH_3$ |
| Cl | $OCH_3$ | $OCH(CH_3)_2$ |
| Cl | $OCH_2CH_2CH_2CH_3$ | $OCH_3$ |
| Cl | $OCH_2CH_2CH_2CH_3$ | $OCH_2CH_3$ |
| Cl | $OCH_2CH_2CH_2CH_3$ | $OCH_2CH_2CH_3$ |
| Cl | $OCH_2CH_2CH_2CH_3$ | $OCH(CH_3)_2$ |
| Cl | $OCH_2CH_2Cl$ | $OCH_3$ |
| Cl | $OCH_2CH_2Cl$ | $OCH_2CH_3$ |
| Cl | $OCH_2CH_2Cl$ | $OCH_2CH_2CH_3$ |
| Cl | $OCH_2CH_2Cl$ | $OCH(CH_3)_2$ |
| Cl | $OCHClCH(CH_3)_2$ | $OCH_3$ |
| Cl | $OCHClCH(CH_3)_2$ | $OCH_2CH_3$ |
| Cl | $OCHClCH(CH_3)_2$ | $OCH_2CH_2CH_3$ |
| Cl | $OCHClCH(CH_3)_2$ | $OCH(CH_3)_2$ |
| Cl | $CF_3$ | $OCH_3$ |
| Cl | $CF_3$ | $OCH_2CH_3$ |
| Cl | $CF_3$ | $OCH_2CH_2CH_3$ |
| Cl | $CF_3$ | $OCH(CH_3)_2$ |
| Cl | $CF_2CF_3$ | $OCH_3$ |
| Cl | $CF_2CF_3$ | $OCH_2CH_3$ |
| Cl | $CF_2CF_3$ | $OCH_2CH_2CH_3$ |
| Cl | $CF_2CF_3$ | $OCH(CH_3)_2$ |
| Cl | $CF_2CF_2H$ | $OCH_3$ |
| Cl | $CF_2CF_2H$ | $OCH_2CH_3$ |
| Cl | $CF_2CF_2H$ | $OCH_2CH_2CH_3$ |
| Cl | $CF_2CF_2H$ | $OCH(CH_3)_2$ |
| Cl | $CH_2Cl$ | $OCH_3$ |
| Cl | $CH_2Cl$ | $OCH_2CH_3$ |
| Cl | $CH_2Cl$ | $OCH_2CH_2CH_3$ |
| Cl | $CH_2Cl$ | $OCH(CH_3)_2$ |
| Cl | $CH_2Br$ | $OCH_3$ |
| Cl | $CH_2Br$ | $OCH_2CH_3$ |
| Cl | $CH_2Br$ | $OCH_2CH_2CH_3$ |
| Cl | $CH_2Br$ | $OCH(CH_3)_2$ |
| Cl | $CH_2CH_2CN$ | $OCH_3$ |
| Cl | $CH_2CH_2CN$ | $OCH_2CH_3$ |
| Cl | $CH_2CH_2CN$ | $OCH_2CH_2CH_3$ |
| Cl | $CH_2CH_2CN$ | $OCH(CH_3)_2$ |
| Cl | $CH_2CH_2CH_2CN$ | $OCH_3$ |
| Cl | $CH_2CH_2CH_2CN$ | $OCH_2CH_3$ |
| Cl | $CH_2CH_2CH_2CN$ | $OCH_2CH_2CH_3$ |
| Cl | $CH_2CH_2CH_2CN$ | $OCH(CH_3)_2$ |
| Cl | $CH_2CH_2CH_2CH_2CN$ | $OCH_3$ |
| Cl | $CH_2CH_2CH_2CH_2CN$ | $OCH_2CH_3$ |
| Cl | $CH_2CH_2CH_2CH_2CN$ | $OCH_2CH_2CH_3$ |
| Cl | $CH_2CH_2CH_2CH_2CN$ | $OCH(CH_3)_2$ |
| Cl | $CH_2OCH_3$ | $OCH_3$ |
| Cl | $CH_2OCH_3$ | $OCH_2CH_3$ |
| Cl | $CH_2OCH_3$ | $OCH_2CH_2CH_3$ |
| Cl | $CH_2OCH_3$ | $OCH(CH_3)_2$ |
| Cl | $C(CH_3)_2OCH_3$ | $OCH_3$ |
| Cl | $C(CH_3)_2OCH_3$ | $OCH_2CH_3$ |
| Cl | $C(CH_3)_2OCH_3$ | $OCH_2CH_2CH_3$ |
| Cl | $C(CH_3)_2OCH_3$ | $OCH(CH_3)_2$ |
| Cl | $CH(CH_3)OCH_3$ | $OCH_3$ |
| Cl | $CH(CH_3)OCH_3$ | $OCH_2CH_3$ |
| Cl | $CH(CH_3)OCH_3$ | $OCH_2CH_2CH_3$ |
| Cl | $CH(CH_3)OCH_3$ | $OCH(CH_3)_2$ |
| Cl | $CH(CH_3)OCH_2CH_3$ | $OCH_3$ |
| Cl | $CH(CH_3)OCH_2CH_3$ | $OCH_2CH_3$ |
| Cl | $CH(CH_3)OCH_2CH_3$ | $OCH_2CH_2CH_3$ |
| Cl | $CH(CH_3)OCH_2CH_3$ | $OCH(CH_3)_2$ |
| Cl | $CH_2OCH_2CH_2CH_3$ | $OCH_3$ |
| Cl | $CH_2OCH_2CH_2CH_3$ | $OCH_2CH_3$ |
| Cl | $CH_2OCH_2CH_2CH_3$ | $OCH_2CH_2CH_3$ |
| Cl | $CH_2OCH_2CH_2CH_3$ | $OCH(CH_3)_2$ |
| Br | $CH_3$ | $OCH_3$ |
| Br | $CH_3$ | $OCH_2CH_3$ |
| Br | $CH_3$ | $OCH_2CH_2CH_3$ |
| Br | $CH_3$ | $OCH(CH_3)_2$ |
| Br | $OCH_2CH_3$ | $OCH_3$ |
| Br | $OCH_2CH_3$ | $OCH_2CH_3$ |
| Br | $OCH_2CH_3$ | $OCH_2CH_2CH_3$ |
| Br | $OCH_2CH_3$ | $OCH(CH_3)_2$ |
| Br | $OCH_3$ | $OCH_3$ |
| Br | $OCH_3$ | $OCH_2CH_3$ |
| Br | $OCH_3$ | $OCH_2CH_2CH_3$ |
| Br | $OCH_3$ | $OCH(CH_3)_2$ |
| F | $CH_3$ | $OCH_3$ |
| F | $CH_3$ | $OCH_2CH_3$ |
| F | $CH_3$ | $OCH_2CH_2CH_3$ |
| F | $CH_3$ | $OCH(CH_3)_2$ |
| F | $OCH_2CH_3$ | $OCH_3$ |
| F | $OCH_2CH_3$ | $OCH_2CH_3$ |
| F | $OCH_2CH_3$ | $OCH_2CH_2CH_3$ |
| F | $OCH_2CH_3$ | $OCH(CH_3)_2$ |
| F | $OCH_3$ | $OCH_3$ |
| F | $OCH_3$ | $OCH_2CH_3$ |
| F | $OCH_3$ | $OCH_2CH_2CH_3$ |
| F | $OCH_3$ | $OCH(CH_3)_2$ |
| I | $CH_3$ | $OCH_3$ |
| I | $CH_3$ | $OCH_2CH_3$ |
| I | $CH_3$ | $OCH_2CH_2CH_3$ |
| I | $CH_3$ | $OCH(CH_3)_2$ |
| I | $OCH_2CH_3$ | $OCH_3$ |
| I | $OCH_2CH_3$ | $OCH_2CH_3$ |
| I | $OCH_2CH_3$ | $OCH_2CH_2CH_3$ |
| I | $OCH_2CH_3$ | $OCH(CH_3)_2$ |
| I | $OCH_3$ | $OCH_3$ |
| I | $OCH_3$ | $OCH_2CH_3$ |
| I | $OCH_3$ | $OCH_2CH_2CH_3$ |
| I | $OCH_3$ | $OCH(CH_3)_2$ |
| Cl | $OCH_2CH_3$ | CN |
| Cl | $CH_3$ | CN |
| Cl | $OCH_3$ | CN |
| Cl | $OCH(CH_3)_2$ | CN |
| Cl | $OCH_2CH_2CH_3$ | CN |
| Cl | $OCH_2CH_2CH_2CH_3$ | CN |
| Cl | $CH_2CH_3$ | CN |
| Cl | $CH_2CH_2CH_3$ | CN |
| Cl | $CH(CH_3)_2$ | CN |
| Cl | $CH_2CH_2CH_2CH_3$ | CN |
| Cl | $CH_2CH(CH_3)_2$ | CN |
| Cl | H | CN |
| Cl | H | $OCH_2CH_3$ |
| Cl | H | $OCH_3$ |
| Cl | H | $OCH(CH_3)_2$ |
| Br | H | CN |
| F | H | CN |
| I | H | CN |
| Br | H | $OCH_2CH_3$ |
| F | H | $OCH_2CH_3$ |
| I | H | $OCH_2CH_3$ |
| Br | H | $OCH_3$ |

TABLE 1-continued

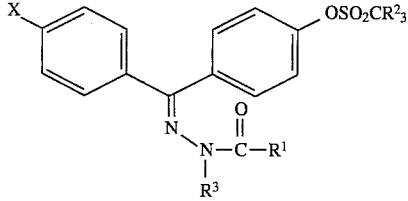

wherein $R^2$ is fluorine, $R^3$ is $CH_2R^4$,
and X, $R^1$ and $R^4$ are each as defined below.

| X | $R^1$ | $R^4$ |
|---|---|---|
| F | H | $OCH_3$ |
| I | H | $OCH_3$ |
| Br | H | $OCH(CH_3)_2$ |
| F | H | $OCH(CH_3)_2$ |
| I | H | $OCH(CH_3)_2$ |
| Br | $OCH_2CH_3$ | CN |

TABLE 2

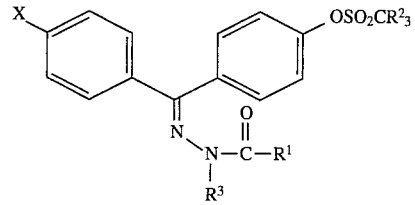

wherein $R^2$ is hydrogen, $R^3$ is $CH_2R^4$,
and X, $R^1$ and $R^4$ are each as defined below.

| X | $R^1$ | $R^4$ |
|---|---|---|
| Cl | $OCH_2CH_3$ | CN |
| Br | $OCH_2CH_3$ | CN |
| Cl | $OCH_2CH_3$ | $OCH_2CH_3$ |
| Br | $OCH_2CH_3$ | $OCH_2CH_3$ |
| Cl | $OCH_3$ | CN |
| Cl | $OCH_3$ | $OCH_2CH_3$ |
| Cl | $OCH_2CH_3$ | $OCH(CH_3)_2$ |
| Cl | $OCH_2CH_3$ | $OCH_3$ |
| Cl | $OCH_3$ | $OCH_3$ |
| Cl | $OCH_3$ | $OCH(CH_3)_2$ |
| Cl | $CH_3$ | CN |
| Cl | $CH_3$ | $OCH_3$ |
| Cl | $CH_3$ | $OCH_2CH_3$ |
| Cl | $CH_3$ | $OCH(CH_3)_2$ |
| Cl | $CH_2CH_3$ | CN |
| Cl | $CH_2CH_3$ | $OCH_3$ |
| Cl | $CH_2CH_3$ | $OCH_2CH_3$ |
| Cl | $CH_2CH_3$ | $OCH(CH_3)_2$ |
| Cl | $CH_2CH_3$ | CN |
| Cl | $CH_2CH_2CH_3$ | $OCH_3$ |
| Cl | $CH_2CH_2CH_3$ | $OCH_2CH_3$ |
| Cl | $CH_2CH_2CH_3$ | $OCH(CH_3)_2$ |

TABLE 3 wherein $R^2$ is fluorine, $R^3$ is $SR^5$,
and X, $R^1$ and $R^5$ are each as defined below.

| X | $R^1$ | $R^5$ |
|---|---|---|
| Cl | $-CH_3$ | $-N(n-C_4H_9)_2$ |
| Cl | $-CH_3$ | $-N(CH_3)CO_2CH_2CH_3$ |
| Cl | $-CH_3$ | $-N(i-C_3H_7)CH_2CH_2CO_2CH_2CH_3$ |
| Cl | $-CH_3$ | $-N(CH_2C_6H_5)CH_2CH_2CO_2CH_2CH_3$ |
| Cl | $-OCH_2CH_3$ | $-N(CH_2C_6H_5)CH_2CH_2CO_2CH_2CH_3$ |
| Cl | $-OCH_2CH_3$ | $-N(CH_3)CO_2CH_2CH_3$ |
| Cl | $-OCH_2CH_3$ | $-N(i-C_3H_7)CH_2CH_2CO_2CH_2CH_3$ |
| Cl | $-OCH_2CH_3$ | $-N(n-C_4H_9)_2$ |
| Cl | $-CH_3$ | $-CCl_3$ |
| Cl | $-OCH_2CH_3$ | $-CCl_3$ |
| Cl | $-H$ | $-2-NO_2-C_6H_4$ |
| Br | $-CH_3$ | $-CH_2CH_2$ |
| F | $-CH_2CH_3$ | $-(CH_2)_4CH_3$ |
| Cl | $-CH_2CH_2CH_2CH_3$ | $-(CH_2)_{10}CH_3$ |
| Cl | $-CF_3$ | $-(CH_2)_{15}CH_3$ |
| Cl | $-CF_2CF_3$ | $-CCl_3$ |
| Cl | $-CH_2CH_2CH_2CH_2Cl$ | $-CClF_2$ |
| Cl | $-CH_3CN$ | $-CH_2Cl$ |
| Cl | $-CH_2CH_2CN$ | $-(CH_2)_5CH_2Cl$ |

TABLE 3-continued $$\text{X}-\text{C}_6\text{H}_4-\text{C}(=\text{N}-\text{N}(\text{R}^3)-\text{C}(=\text{O})-\text{R}^1)-\text{C}_6\text{H}_4-\text{OSO}_2\text{CR}^2{}_3$$

wherein $R^2$ is fluorine, $R^3$ is $SR^5$,
and X, $R^1$ and $R^5$ are each as defined below.

| X | $R^1$ | $R^5$ |
|---|---|---|
| Cl | —CH₂CH₂CH₂CH₂CN | —(CH₂)₁₅CH₂F |
| Cl | —CH₂OCH₃ | —C₆H₅ |
| Cl | —CH₂CH₂OCH₃ | -4-CH₃—C₆H₄ |
| Cl | —CH₂CH₂CH₂CH₂OCH₃ | -4-CH₂CH₃—C₆H₄ |
| Cl | —CH₂OCH₂CH₃ | -4-(CH₂)₅CH₃—C₆H₄ |
| Cl | —CH₂CH₂OCH₂CH₂CH₃ | -4-(CH₂)₉CH₃—C₆H₄ |
| Cl | —CH₂O—CH(CH₃)₂ | -4-(CH₂)₅CH₃—C₆H₄ |
| Cl | —CH₂OCH₂CH₂CH₂CH₃ | -4-Cl—C₆H₄ |
| Cl | —(CH₂)₄—O—(CH₂)₃—CH₃ | -4-F—C₆H₄ |
| Cl | —OCH₃ | -4-Br—C₆H₄ |
| Cl | —OCH₂CH₃ | -2,4-Cl₂C₆H₃ |
| Cl | —OCH₂CH₂CH₂CH₃ | -2-NO₂—C₆H₄ |
| Cl | —OCH₂(CH₃)CH₂CH₃ | -4-NO₂—C₆H₄ |
| Cl | —OCH₂CH₂Cl | -2,4-(NO₂)₂—C₆H₃ |
| Cl | —OCH₂CH₂CH₂Cl | -2-(NO₂)-4-Cl—C₆H₃ |
| Cl | —CH₃ | —N(CH₂CH₃)₂ |
| Cl | —CH₂CH₃ | —N(CH₃)[(CH₂)₅CH₃] |
| Cl | —CF₃ | —N(CH₃)[(CH₂)₁₀CH₃] |
| Cl | —CF₂CF₃ | —N(CH₃)[(CH₂)₁₅CH₃] |
| Cl | —CH₂CN | —N[(CH₂)₁₀CH₃]₂ |
| Cl | —CH₂OCH₃ | —N(CH₃)CH₂CN |
| Cl | —CH₂OCH₂CH₃ | —N(CH₃)CH₂CH₂CN |
| Cl | —OCH₃ | —N(CH₃)[(CH₂)₅CN] |
| Cl | —OCH₂CH₂CH₃ | —N(CH₃)[(CH₂)₁₀CN] |
| Cl | —OCH₂CH₂Cl | —N(CH₃)[(CH₂)₁₅CN] |
| Cl | —CH₃ | —N(CH₃)CH₂CH₂Cl |
| Cl | —CH₂CH₃ | —N(CH₃)[(CH₂)₅Cl] |
| Cl | —CF₃ | —N(CH₃)[(CH₂)₁₀Cl] |
| Cl | —CF₂CF₃ | —N(CH₃)[(CH₂)₁₅Cl] |
| Cl | —CH₂CN | —N(CH₃)[(CH₂)₁₀F] |
| Cl | —CH₂OCH₃ | —N(CH₂CN)₂ |
| Cl | —CH₂OCH₂CH₃ | —N(CH₂CH₂CN)₂ |
| Cl | —OCH₃ | —N(CH₂CH₂Cl)₂ |
| Cl | —OCH₂CH₂CH₂CH₃ | —N(CH₃)CH₂OCH₃ |
| Cl | —OCH₂CH₂Cl | —N(CH₃)CH₂CH₂OCH₃ |
| Cl | —CH₃ | —N(CH₃)CH₂CH₂CH₂OCH₃ |
| Cl | —CH₂CH₃ | —N(CH₃)[(CH₂)₁₀OCH₃] |
| Cl | —CF₃ | —N(CH₃)[(CH₂)₁₅OCH₃] |
| Cl | —CF₂CF₃ | —N(CH₃)[(CH₂)₃O(CH₂)₅CH₃] |
| Cl | —CH₂CN | —N(CH₃)[(CH₂)₃O(CH₂)₁₀CH₃] |
| Cl | —CH₂OCH₃ | —N(CH₃)[(CH₂)₃O(CH₂)₁₅CH₃] |
| Cl | —CH₂OCH₂CH₃ | —N(CH₂CH₂OCH₃)₂ |
| Cl | —OCH₃ | —N(CH₂CH₂CH₂OCH₃)₂ |
| Cl | —OCH₂CH₂CH₂CH₃ | —N(CH₃)CH₂CH=CH₂ |
| Cl | —OCH₂CH₂Cl | —N(CH₃)CH₂CH=CHCH₃ |
| Cl | —CH₃ | —N(CH₃)CH₂CH=CH(CH₂)₁₀CH₃ |
| Cl | —CH₂CH₃ | —N(CH₃)CH₂CH=CH(CH₂)₁₂CH₃ |
| Cl | —CF₂CF₃ | —N(CH₃)CH₂CH=CHCl |
| Cl | —CH₂CN | —N(CH₃)CH₂CH=CCl₂ |
| Cl | —CH₂OCH₃ | —N(CH₃)CH₂CH=CH(CH₂)₅CH₂Cl |
| Cl | —CH₂OCH₂CH₃ | —N(CH₃)CH₂CH=CH(CH₂)₁₂CH₂Cl |
| Cl | —OCH₃ | —N(CH₂CH=CH₂)₂ |
| Cl | —OCH₂CH₂CH₂CH₃ | —N(CH₂CH=CHCH₃)₂ |
| Cl | —OCH₂CH₂Cl | —N(CH₂CH=CCl₂)₂ |
| Cl | —CH₂ | —N(CH₃)CH₂C≡CH |
| Cl | —CH₂CH₃ | —N(CH₃)CH₂C≡CCH₃ |
| Cl | —CF₃ | —N(CH₃)CH₂C≡C(CH₂)₅CH₃ |

TABLE 3-continued

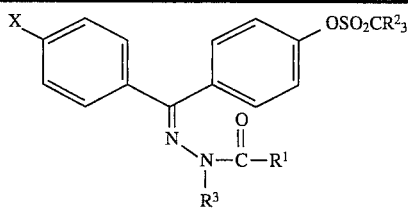

wherein $R^2$ is fluorine, $R^3$ is $SR^5$,
and X, $R^1$ and $R^5$ are each as defined below.

| X | $R^1$ | $R^5$ |
|---|---|---|
| Cl | $-CF_2CF_3$ | $-N(CH_3)CH_2C \equiv C(CH_2)_{12}CH_3$ |
| Cl | $-CH_2CN$ | $-N(CH_3)CH_2C \equiv CH$ |
| Cl | $-CH_2OCH_3$ | $-N(CH_3)CH_2C \equiv C(CH_2)_5Cl$ |
| Cl | $-CH_2OCH_2CH_3$ | $-N(CH_3)CH_2C \equiv C(CH_2)_{13}Cl$ |
| Cl | $-OCH_3$ | $-N[CH_2C \equiv C(CH_2)_5Cl]_2$ |
| Cl | $-CH_3$ | $-N(CH_3)C_6H_5$ |
| Cl | $-CH_2CH_3$ | $-N(CH_3)-4-Cl-C_6H_4$ |
| Cl | $-CF_3$ | $-N(CH_3)-4-F-C_6H_4$ |
| Cl | $-CF_2CF_3$ | $-N(CH_3)-2,4-Cl_2-C_6H_3$ |
| Cl | $-CH_2CN$ | $-N(CH_3)-3,5-Cl_2-C_6H_3$ |
| Cl | $-CH_2OCH_3$ | $-N(CH_3)-4-CH_3-C_6H_4$ |
| Cl | $-CH_2OCH_2CH_3$ | $-N(CH_3)-4-(CH_2)_4CH_3-C_6H_4$ |
| Cl | $-OCH_3$ | $-N(CH_3)-4-(CH_2)_9CH_3-C_6H_4$ |
| Cl | $-OCH_2CH_2CH_2CH_3$ | $-N(CH_3)-4-CF_3-C_6H_4$ |
| Cl | $-OCH_2CH_2Cl$ | $-N(CH_3)-4-(CH_2)_4CH_2Cl-C_6H_4$ |
| Cl | $-CH_3$ | $-N(CH_3)-4-(CH_2)_9CH_2Cl-C_6H_4$ |
| Cl | $-CH_2CH_3$ | $-N(CH_3)CH_2C_6H_5$ |
| Cl | $-CF_3$ | $-N(CH_3)CH_2CH_2C_6H_5$ |
| Cl | $-CF_2CF_3$ | $-N(CH_3)CH_2CH_2CH_2C_6H_5$ |
| Cl | $-CH_2CN$ | $-N(CH_3)CH_2-(4-CH_3CH_2-C_6H_4)$ |
| Cl | $-CH_2OCH_3$ | $-N(CH_3)CH_2CH_2-[4-CH_3(CH_2)_9C_6H_4]$ |
| Cl | $-CH_2OCH_2CH_3$ | $-N(CH_2C_6H_5)_2$ |
| Cl | $-OCH_3$ | $-N(CH_2CH_2C_6H_5)_2$ |
| Cl | $-OCH_2CH_2CH_2CH_3$ | $-N(CH_3)CH_2-4-Cl-C_6H_4$ |
| Cl | $-OCH_2CH_2Cl$ | $-N(CH_3)CH_2CH_2-4-Cl-C_6H_4$ |
| Cl | $-CH_3$ | $-N(CH_3)CH_2-4-CF_3-C_6H_4$ |
| Cl | $-CH_2CH_3$ | $-N(CH_3)CH_2CH_2-4-CF_3-C_6H_4$ |
| Cl | $-CF_3$ | $-N(CH_2-4-CF_3-C_6H_4)_2$ |
| Cl | $-CF_2CF_3$ | $-N(CH_3)CO_2CH_3$ |
| Cl | $-CH_2CN$ | $-N(CH_3)CO_2CH_2CH_3$ |
| Cl | $-CH_2OCH_3$ | $-N(CH_3)CO_2CH(CH_3)_2$ |
| Cl | $-CH_2OCH_2CH_3$ | $-N(CH_3)CO_2(CH_2)_3-CH_3$ |
| Cl | $-OCH_3$ | $-N(CH_3)CO_2(CH_2)_{10}CH_3$ |
| Cl | $-OCH_2CH_2CH_2CH_3$ | $-N(CH_3)CO_2(CH_2)_{14}CH_3$ |
| Cl | $-OCH_2CH_2Cl$ | $-N(CH_3)CH_2CO_2CH_3$ |
| Cl | $-CH_3$ | $-N(CH_3)CH_2CH_2CO_2CH_2CH_3$ |
| Cl | $-CH_2CH_3$ | $-N(CH_3)CH_2CH_2CH_2CO_2CH_2CH_3$ |
| Cl | $-CF_3$ | $-N(CH_3)CH_2CO_2(CH_2)_5CH_3$ |
| Cl | $-CF_2CF_3$ | $-N(CH_3)CH_2CH_2CO_2(CH_2)_{12}CH_3$ |
| Cl | $-OCH_2CH_3$ | $-N[(CH_2)_3CH_3]CH_2CH_2-CO_2CH_2CH_3$ |
| Cl | $-OCH_2CH_3$ | $-N[CH(CH_3)_2]CH_2C_6H_5$ |
| Cl | $-OCH_2CH_3$ | $-N(CH_2CN)CH_2CH_2CO_2CH_2CH_3$ |
| Cl | $-OCH_2CH_3$ | $-N[CH(CH_3)_2]CH_2CN$ |
| Cl | $-OCH_2CH_3$ | $-N(CH_2CH_3)CH_2CN$ |
| Cl | $-OCH_2CH_3$ | $-N(CH_2CN)CH_2CH_2C_6H_5$ |
| Cl | $-OCH_2CH_3$ | $-CCl_3$ |
| Cl | $-OCH_2CH_3$ | $-CH_3$ |
| Cl | $-OCH_2CH_3$ | $-CH_2Cl$ |
| Cl | $OCH_2CH_3$ | $-N(n-C_3H_7)_2$ |
| Cl | $OCH_2CH_3$ | $-N(i-C_3H_7)_2$ |
| Cl | $OCH_2CH_3$ | $-N(n-C_4H_9)_2$ |
| Cl | $OCH_2CH_3$ | $-N(i-C_4H_9)_2$ |
| Cl | $OCH_2CH_3$ | $-N(sec-C_4H_9)_2$ |
| Cl | $OCH_2CH_3$ | $-N(n-C_6H_{13})_2$ |
| Cl | $OCH_2CH_3$ | $-N(n-C_8H_{17})_2$ |

TABLE 3-continued wherein $R^2$ is fluorine, $R^3$ is $SR^5$,
and X, $R^1$ and $R^5$ are each as defined below.

| X | $R^1$ | $R^5$ |
|---|---|---|
| Cl | $OCH_2CH_3$ | $-N(CH_2CO_2CH_3)_2$ |
| Cl | $OCH_2CH_3$ | $-N(CH_2CO_2C_2H_5)_2$ |
| Cl | $OCH_2CH_3$ | $-N(CH_2CO_2-n-C_3H_7)_2$ |
| Cl | $OCH_2CH_3$ | $-N(CH_2CO_2-n-C_4H_9)_2$ |
| Cl | $OCH_2CH_3$ | $-N(CH_2CN)_2$ |
| Cl | $OCH_2CH_3$ | $-N(CH_2CH_2CO_2CH_3)_2$ |
| Cl | $OCH_2CH_3$ | $-N(CH_2CH_2CO_2C_2H_5)_2$ |
| Cl | $OCH_2CH_3$ | $-N(CH_2CH_2CO_2-n-C_4H_9)_2$ |
| Cl | $OCH_2CH_3$ | $-N(CH_2CH_2CN)_2$ |
| Cl | $OCH_2CH_3$ | $-N(CH_2CN)CO_2CH_3$ |
| Cl | $OCH_2CH_3$ | $-N(CH_2CN)CO_2C_2H_5$ |
| Cl | $OCH_2CH_3$ | $-N(CH_2CN)CO_2-n-C_4H_9$ |
| Cl | $OCH_2CH_3$ | $-N(CH_2CN)CH_2CO_2CH_3$ |
| Cl | $OCH_2CH_3$ | $-N(CH_2CN)CH_2CO_2C_2H_5$ |
| Cl | $OCH_2CH_3$ | $-N(CH_2CN)CH_2CO_2-n-C_4H_9$ |
| Cl | $OCH_2CH_3$ | $-N(CH_2CN)CH_2CH_2CO_2-n-C_4H_9$ |
| Cl | $OCH_2CH_3$ | $-N(C_2H_5)CO_2C_2H_5$ |
| Cl | $OCH_2CH_3$ | $-N(n-C_3H_7)CO_2C_2H_5$ |
| Cl | $OCH_2CH_3$ | $-N(i-C_3H_7)CO_2C_2H_5$ |
| Cl | $OCH_2CH_3$ | $-N(n-C_4H_9)CO_2C_2H_5$ |
| Cl | $OCH_2CH_3$ | $-N(n-C_6H_{13})CO_2C_2H_5$ |
| Cl | $OCH_2CH_3$ | $-N(n-C_8H_{17})CO_2C_2H_5$ |
| Cl | $OCH_2CH_3$ | $-N(C_2H_5)CH_2CO_2CH_3$ |
| Cl | $OCH_2CH_3$ | $-N(C_2H_5)CH_2CO_2C_2H_5$ |
| Cl | $OCH_2CH_3$ | $-N(i-C_3H_7)CH_2CO_2-n-C_4H_9$ |
| Cl | $OCH_2CH_3$ | $-N(n-C_4H_9)CH_2CO_2C_2H_5$ |
| Cl | $OCH_2CH_3$ | $-N(C_2H_5)CH_2CH_2CO_2CH_3$ |
| Cl | $OCH_2CH_3$ | $-N(C_2H_5)CH_2CH_2CO_2C_2H_5$ |
| Cl | $OCH_2CH_3$ | $-N(C_2H_5)CH_2CH_2CO_2-n-C_4H_9$ |
| Cl | $OCH_2CH_3$ | $-N(i-C_3H_7)CH_2CH_2CO_2CH_3$ |
| Cl | $OCH_2CH_3$ | $-N(i-C_3H_7)CH_2CH_2CO_2C_2H_5$ |
| Cl | $OCH_2CH_3$ | $-N(i-C_3H_7)CH_2CH_2CO_2-n-C_3H_7$ |
| Cl | $OCH_2CH_3$ | $-N(i-C_3H_7)CH_2CH_2CO_2-i-C_3H_7$ |
| Cl | $OCH_2CH_3$ | $-N(i-C_3H_7)CH_2CH_2CO_2-n-C_4H_9$ |
| Cl | $OCH_2CH_3$ | $-N(i-C_3H_7)CH_2CH_2CO_2-n-C_6H_{13}$ |
| Cl | $OCH_2CH_3$ | $-N(i-C_3H_7)CH_2CH_2CO_2-n-C_8H_{17}$ |
| Cl | $OCH_2CH_3$ | $-N(i-C_3H_7)CH_2CH_2CO_2-n-C_{12}H_{25}$ |
| Cl | $OCH_2CH_3$ | $-N(CH_2CH_2Cl)CH_2CH_2CO_2C_2H_5$ |
| Cl | $OCH_2CH_3$ | $-N(CH_2CH_2CH_2OCH_3)CH_2CH_2-CO_2C_2H_5$ |
| Cl | $CH_2CH_3$ | $-N(n-C_4H_9)CH_2CO_2C_2H_5$ |
| Cl | $CH_2CH_3$ | $-N(C_2H_5)CH_2CH_2CO_2CH_3$ |
| Cl | $CH_2CH_3$ | $-N(C_2H_5)CH_2CH_2CO_2C_2H_5$ |
| Cl | $CH_2CH_3$ | $-N(C_2H_5)CH_2CH_2CO_2-n-C_4H_9$ |
| Cl | $CH_2CH_3$ | $-N(i-C_3H_7)CH_2CH_2CO_2CH_3$ |
| Cl | $CH_2CH_3$ | $-N(i-C_3H_7)CH_2CH_2CO_2C_2H_5$ |
| Cl | $CH_2CH_3$ | $-N(i-C_3H_7)CH_2CH_2CO_2-n-C_3H_7$ |
| Cl | $CH_2CH_3$ | $-N(i-C_3H_7)CH_2CH_2CO_2-i-C_3H_7$ |
| Cl | $CH_2CH_3$ | $-N(i-C_3H_7)CH_2CH_2CO_2-n-C_4H_9$ |
| Cl | $CH_2CH_3$ | $-N(i-C_3H_7)CH_2CH_2CO_2-n-C_6H_{13}$ |
| Cl | $CH_2CH_3$ | $-N(i-C_3H_7)CH_2CH_2CO_2-n-C_8H_{17}$ |
| Cl | $CH_2CH_3$ | $-N(i-C_3H_7)CH_2CH_2CO_2-n-C_{12}H_{25}$ |
| Cl | $CH_2CH_3$ | $-N(CH_2CH_2Cl)CH_2CH_2CO_2C_2H_5$ |
| Cl | $CH_2CH_3$ | $-N(CH_2CH_2CH_2OCH_3)CH_2CH_2-CO_2C_2H_5$ |
| Cl | $CH_3$ | $-N(n-C_4H_9)CH_2CO_2C_2H_5$ |
| Cl | $CH_3$ | $-N(C_2H_5)CH_2CH_2CO_2CH_3$ |
| Cl | $CH_3$ | $-N(C_2H_5)CH_2CH_2CO_2C_2H_5$ |
| Cl | $CH_3$ | $-N(C_2H_5)CH_2CH_2CO_2-n-C_4H_9$ |
| Cl | $CH_3$ | $-N(i-C_3H_7)CH_2CH_2CO_2CH_3$ |
| Cl | $CH_3$ | $-N(i-C_3H_7)CH_2CH_2CO_2C_2H_5$ |
| Cl | $CH_3$ | $-N(i-C_3H_7)CH_2CH_2CO_2-n-C_3H_7$ |
| Cl | $CH_3$ | $-N(i-C_3H_7)CH_2CH_2CO_2-i-C_3H_7$ |
| Cl | $CH_3$ | $-N(i-C_3H_7)CH_2CH_2CO_2-n-C_4H_9$ |
| Cl | $CH_3$ | $-N(i-C_3H_7)CH_2CH_2CO_2-n-C_6H_{13}$ |
| Cl | $CH_3$ | $-N(i-C_3H_7)CH_2CH_2CO_2-n-C_8H_{17}$ |

TABLE 3-continued

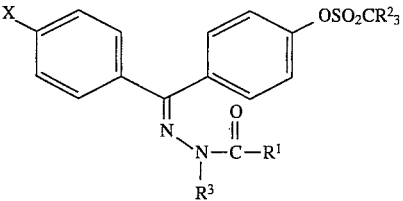

wherein R² is fluorine, R³ is SR⁵,
and X, R¹ and R⁵ are each as defined below.

| X | R¹ | R⁵ |
|---|----|-----|
| Cl | CH₃ | $-N(i\text{-}C_3H_7)CH_2CH_2CO_2-n\text{-}C_{12}H_{25}$ |
| Cl | CH₃ | $-N(CH_2CH_2Cl)CH_2CH_2CO_2C_2H_5$ |
| Cl | CH₃ | $-N(CH_2CH_2CH_2OCH_3)CH_2CH_2-CO_2C_2H_5$ |
| Cl | CH₃ | 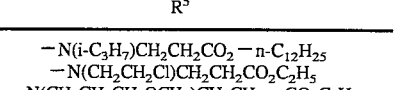 |
| Cl | CH₃ | 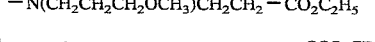 |
| Cl | OCH₂CH₃ | 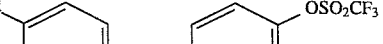 |
| Cl | OCH₂CH₃ | 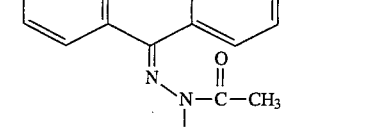 |
| Cl | OCH₂CH₃ |  |

The hydrazone compound of the present invention is effective for controlling various harmful insects including:

Hemiptera:
Delphacidae (planthoppers) such as *Laodelphax striatellus*, *Nilaparvata lugens* and *Sogatella furcifera*; Deltocephalidae (leaf hoppers) such as *Nephotettix cincticeps* and *Nephotettix virescens*, Aphididae (aphids) including *Aphis grossypii*, Pentatomidae (stink bugs), Aleyrodidae, Coccidae (scale insects), Tingidae (lace bugs), Psyllidae (jumping plant-lices), etc.;

Lepidoptera:
Pyralidae such as *Chilo suppressalis*, *Cnaphalocrocis medinalis*, *Ostrinia nubilalis*, *Parapediasia teterrella*, *Notarcha derogata* and *Plodia interpunctella*; Noctuidae (owlet moths) such as *Spodoptera litura*, *Pseudaletia separata*, *Mamestra brassicae*, *Agrotis ipsilon*, Heliothis moths, Helicoverpa moths; Pieridac such as *Pieris rapae crucivora*; Tortricidae (bell moths) such as *Grapholita molesta* and *Cydia pornonella*, *Carposina niponensis*, Lyonetiidae (leaf mining moths), Euproctis and Lymantria (gypsy) moths; Yponomeutidae such as *Plutella xylostella*; Gelechiidae such as *Pectinophora gossypiella*, Arctiidae such as *Hyphantria cunea*, *Tinea translucens*, *Tineoia bisselliella*, etc.;

Diptera:
Culex (house mosquitos) such as *Culex pipiens pallens* and *Cules tritaeniorhynchus*; Aedes such as *Aedes albopictus* and *Aedes aegypti*; Anophelinae such as *Anophelinae sinensis*, Chironomidae (midges); Muscidae such as *Musca domestica* (house fly) and *Muscina stabulans*; Calliphoridae (blow flies); Sarcophagidae (flesh flies); Anthomyiidae such as *Delia Platura* and *Delia antigua*, Trypetidae (fruit flies), Drosophilidae (wine flies), Psychodidae (moth flies), Tabanidae (deer flies), Simuliidae (black flies), Stomoxyinae, Agromyzidae (leaf miner flies), etc.;

Coleoptera (Beetles):
Diabrotica (corn rootworms) such as *Diabrotica virgifera* and *Diabrotica undecirnpunctata*; Scarabaeidae such as *Anomala cuprea* and *Anomala rufocuprea*; Curculionidae (snout beetles) such as *Sitophilus zeamais* (grain weevils) *Lissorphoptrus oryzophilus, Hypera pastica,* and *Calosobruchys chinensis, Neatus ventraiis* (darkling beetles) such as *Tenebrio molitor* and *Tribolium castaneum*; Chrysomelidae (leaf beetles) such as *Aulacophora femoralis, Leptinotarsa decemlineata* and *Phyllotreta striolata*; Anobiidae (death-watch beetles), Epilachna spp. such as *Henosepilachna vigintioctopunctata,* Lyctidae (powder-post beetles), Bostrychidae (lesser grain borers), *Paederus fuscipes,* etc.;

Blattaria (Cockroaches):
*Blattella germanica* (croton bugs), *Periplaneta fuliginosa, Periplaneta americana, Periplaneta brunnea, Blatta orientalis,* etc.;

Thysanoptera (Thrips):
*Thrips palmi, Thrips tabaci, Thrips hawaiiensis,* etc.;

Hymenoptera:
Formicidae (ants), Vespa (hornets), Bethylidae (bethylid wasps), Tenthredinoidae (sawflies) such as *Athalia rosae japonensis* (cabbage sawfly), etc.;

Orthoptera:
Gryllotalpa (mole crickets), Acrididae (grasshoppers), etc.;

Siphonaptera (Fleas):
*Purex irritans,* etc.;

Anoplura (Sucking Louses):
*Pediculus humanus capitis, Phthirus pubis,* etc.;

Isoptera (Termites):
*Reticulitermes speratus, Coptotermes formosanus,* etc.

The hydrazone compound of the present invention is also effective for various harmful insects having resistance to conventional insecticides.

When the hydrazone compound of the present invention is used as an active ingredient of insecticides, it may be used as such without addition of any other ingredients. The hydrazone compound of the present invention is, however, usually formulated into a dosage for in such as oil sprays, emulsifiable concentrates, wettable powders, flowables, granules, dusts, aerosols, fumigants (foggings) and poison baits. These formulations are usually prepared by mixing the hydrazone compound of the present invention with a solid carrier, a liquid carrier, a gaseous carrier or a bait, and if necessary, adding a surfactant and other auxiliaries for the formulation. These formulations usually contain the hydrazone compound of the present invention as an active ingredient in an amount of 0.01% to 95% by weight.

Examples of the solid carrier to be used for the formulation are fine powder or granules of clay such as kaolin clay, diatomaceous earth, synthetic hydrated silicon oxide, bentonite, Fubasami clay and acid clay; various kinds of talc, ceramics, other inorganic minerals such as sericite, quartz, sulfur, active carbon, calcium carbonate and hydrated silica; and chemical fertilizers such as ammonium sulfate, ammonium phosphate, ammonium nitrate, urea and ammonium chloride.

Examples of the liquid carrier are water; alcohols such as methanol and ethanol; ketones such as acetone and methyl ethyl ketone; aromatic hydrocarbons such as benzene, toluene, xylene, ethylbenzene and methylnaphthalene; aliphatic hydrocarbons such as hexane, cyclohexane, kerosine and gas oil; esters such as ethyl acetate and butyl acetate; nitriles such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane and carbon tetrachloride; dimethyl sulfoxide; and vegetable oils such as soybean oil and cottonseed oil.

Examples of the gaseous carrier or propellant are CFCs (chlorofluorocarbons), butane gas, LPG (liquefied petroleum gas), diethyl ether and carbon dioxide.

Examples of the surfactant are alkyl sulfates, alkyl sulfonates, alkyl arylsulfonates, alkyl aryl ethers and their polyoxyethylene derivatives, polyethylene glycol ethers, polyhydric alcohol esters and sugar alcohol derivatives.

Examples of the auxiliaries for the formulation, such as fixing agents or dispersing agents, are casein, gelatin, polysaccharides such as starch, gum arabic, cellulose derivatives and alginic acid, lignin derivatives, bentonite, sugars, and synthetic watersoluble polymers such as polyvinyl alcohol, polyvinyl pyrrolidone and polyacrylic acid.

Examnples of the stabilizer are PAP (isopropyl acid phosphate), BHT (2,6-di-tert-butyl-4-methylphenol), BHA (mixtures of 2-t-butyl-4-methoxyphenol and 3-tert-butyl-4-methoxyphenol), vegetable oils, mineral oils, surfactants, fatty acids and their esters.

Examples of the base material to be used in the poison baits are bait materials such as grain powder, vegetable oils, sugars and crystalline cellulose; antioxidants such as dibutylhydroxytoluene and nordihydroguaiaretic acid; preservatives such as dehydroacetic acid; substances for preventing erroneous eating, such as red pepper powder, attractant flavors such as cheese flavor or onion flavor.

The formulation thus obtained is used as such or after dilution with water. The formulation may also be used in combination with other insecticides, acaricides, nematocides, bactericides, fungicides, herbicides, plant growth regulators, synergists, fertilizers, soil conditioners and/or animal feed under non-mixing conditions or premixing conditions.

Examples of the insecticide, acaricide and/or nematocide which can be used are organophosphorus compounds such as Fenitrothion [(O,O-dimethyl O-(3-methyl-4-nitrophenyl)phosphorothioate], Fenthion [O,O-dimethyl O-(3-methyl-4-methylthio)phenyl)phophorothioate], Diazinon [O,O-diethyl-O-2-isopropyl-6-methylpyrimidin-4-ylphosphorothioate], Chlorpyriphos [O,O-diethyl-O-3,5,6-trichloro-2-pyridylphosphorothioate], Acephate [O,S-dimethylacetylphosphoramidothioate], Methidachion [S-2,3-dihydro-5-methoxy-2-oxo-1,3,4-thiadiazol-3-ylmethyl O,O-dimethylphosphorodithioate], Disulfoton [O,O-diethyl S-2-ethylthioethylphosphorothioate], DDVP [2,2-dichlorovinyldimethylphosphate], Sulprofos [O-ethyl O-4-(methylthio)phenyl S-propyl phosphorodithioate], Cyanophos [O-4-cyanophenyl O,O-dimethylphosphorothioate], Dioxabenzofos [2-methoxy-4H-1,3,2-benzodioxaphosphinin-2-sulfide], Dimethoate [O,O-dimethyl-S-(N-methylcarbamoylmethyl)dithiophosphate], Phenthoate [ethyl 2-dimethoxyphosphinothioylthio(phenyl)acetate], Malathion [diethyl(dimethoxyphosphinothioylthio)succinate], Trichlorfon [dimethyl 2,2,2-trichloro-1-hydroxyethylphosphonate], Azinphos-methyl [S-3,4-dihydro-4-oxo-1,2,3-benzotriazin-3-ylmethyl-O,O-dimethylphosphorodithioate], Monocrotophos [dimethyl (E)-1-methyl-2-(methylcarbamoyl)vinylphosphate] and Ethion [O,O,O', O'-tetraethyl S,S'-methylenebis(phosphorodithioate)]; carbamate compounds such as BPMC [2-sec-butylphenylmethylcarbamate], Benfuracarb [ethyl N-[2,3-dihydro-2,2-dimethylbenzofuran-7-yloxycarbonyl(methyl)aminothio]-N-isopropyl-β-alaninate], Propoxur [2-isopropoxyphenyl N-methylcarbamate], Carbosulfan [2,3-dihydro-2,2-dimethyl7-benzo[b]furanyl N-dibutylaminothio-N-methylcarbamate], Carbaril [1-naphthyl-N-methylcarbamate], Methomyl [S-methyl-N-[(methylcarbamoyl)oxy]

thioacetoimidate], Ethiofencarb [2-(ethylthiomethyl)phenylmethylcarbamate], Aldicarb [2-methyl-2-(methylthio)-propanaldehyde O-methylcarbamoyloxime], Oxamyl [N,N-dimethyl-2-methylcarbamoyl-oxyimino-2-(methylthio)acetamide] and Fenothiocarb [S-4ophenoxybutyl)-N,N-dimethyl-thiocarbamate]; pyrethroid compounds such as Etofenprox [2-(4-ethoxyphenyl)-2-methyl-propyl-3-phenoxybenzylether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclopropanecarboxylate], Cypermethrin [(RS)-α-cyano-3-phenoxybenzyl (1RS,3RS)-3-(2,2-dichlorovinyl)-2,2-dimethylcyclopropanecarboxylate], Permethrin [3-phenoxybenzyl (1RS,3RS)-3-(2,2-dichlorovinyl)-2,2-dimethylcyclopropanecarboxylate], Cyhalothrin [(RS)-α-cyano-3-phenoxybenzyl (Z)-(1RS,3RS)-3-(2-chloro-3,3,3-trifluoropropenyl)-2,2-dimethylcyclopropanecarboxylate], Deltamethrin [(S)-α-cyano-m-phenoxybenzyl (1R,3R)-3-(2,2-dibromovinyl)-2,2-dimethylcyclopropanecarboxylate], Cycloprothrin [(RS)-α-cyano-3-phenoxybenzyl (RS)-2,2-dichloro- 1-(4-ethoxyphenyl)cyclopropanecarboxylate], Fluvalinate [α-cyano-3-phenoxybenzyl N-(2-chloro-α,α,α-trifluoro-ptolyl)-D-valinate], Bifenthrin [2-methylbiphenyl-3-ylmethyl)(Z)-( 1RS)-cis-3-(2-chloro-3,3,3-trifluoropropen-1-yl)-2,2-dimethylcyclopropanecarboxylate], Acrinathrin [cyano-(3-phenoxyphenyl)methyl [1R-{1α(S*),3α(Z)}]-2,2-dimethyl-3-[3-oxo-3-(2,2,2-trifluoro-1-(trifluoromethyl)ethoxy-1-propenyl]cyclopropanecarboxylate], 2-methyl-2-(4-bromodifluoromethoxyphenyl)propyl (3-phenoxybenzyl) ether, Trarometrin [(S)-α-cyano-3phenoxylbenzyl (1R,3R)-3-[(1'RS)(1',1',2',2'-tetrabromoethyl)]-2,2-dimethylcyclopropanecarboxylate] and Silafluofen [4-ethoxylphenyl [3-(4-fluoro-3-phenoxyphenyl)propyl] dimethylsilane]; thiadiazine derivatives such as Buprofezin [2-tert-butylimino-3-isopropyl-5-phenyl-1,3,5-thiadiazin-4-one]; nitroimidazolidine derivatives such as Imidacloprid [1-(6-chloro-3-pyridylmethyl)-N-nitroimidazolidin-2-ylidenamine]; Nereistoxin derivatives such as Cartap [S,S'-(2-dimethylaminotrimethylene)bisthiocarbamate], Thiocyclam [N,N-dimethyl-1,2,3-trithian-5-ylamine] and Bensultap [S,S'-2-dimethylaminotrimethylene di(benzenethiosulfonate)]; N-cynoamidine derivatives such as NI-25 [N-cyano-N'-methyl-N'-(6-chloro-3-pyridylmethyl)acetamidine]; chlorinated hydrocarbons such as Endosulfan [6,7,8,9,10,10-hexachloro-1,5,5a,6,9,9a-hexahydro-6,9-methano- 2,4,3-benzodioxathiepinoxide], γ-BHC [1,2,3,4,5,6-hexachlorocyclohexane] and Kelthane [1,1-bis(chlorophenyl)-2,2,2-trichloroethanol]; benzoylphenylurea compounds such as Chlorfluazuron [1-(3,5-dichloro-4-(3-chloro-5-trifluoromethylpyridin-2-yloxy)phenyl)-3-(2,6-difluorobenzoyl)urea], Teflubenzuron [1-(3,5-dichloro-2,4-difluorophenyl)-3-(2,6-difluorobenzoyl)urea] and Fulphenoxron [1-(4-(2-chloro-4-trifluoromethylphenoxy)-2-fluorophenyl)-3-(2,6-difluorobenzoyl)urea]; formamidine derivatives such as Amitraz [N,N'-[(methylimino)dimethylidine]-di-2,4-xylidine] and Chlordimeform [N'-(4-chloro-2-methylphenyl)-N,N-dimethylmethanimidamide]; thiourea derivatives such as Diafenthiuron [N-(2,6-diisopropyl-4-phenoxyphenyl)-N'-tert-butylcarbodiimide]; Fipronyl [5-amino-1-(2,6-dichloro-α,α,α-trifluoro-p-tolytoly)-4-trifluoromethylsulfinylpyrazole-3-carbonitrite], Tebfenozide [N-tert-butyl-N'-(4-ethylbenzoyl)-3,5-dimethylbenzohydrazide], 4-bromo-2-(4-chlorophenyl)-1-ethoxymethyl-5-trifluoromethylpyrrole-3-carbonitrile, Bromopropylate [isopropyl 4,4'-dibromobenzylate], Tetradifon [4-chlorophenyl2,4,5-trichlorophenyl sulfone], Quinomethionate [S,S-6-methylquinoxaline-2,3-diyldithiocarbonate], Propargite [2-(4-tert-butylphenoxy)cyclohexyl prop-2-yl sulfite], Fenbutalin oxide [bis[tris(2-methyl-2-phenylpropyl)tin)oxide], Hexythiazox [(4RS,5RS)-5-(4-chlorophenyl)-N-chlorohexyl-4-methyl-2-oxo-1,3-thiazolidine-3-carboxamide], Chlofentezine [3,6-bis(2-chlorophenyl)-1,2,4,5-tetrazine], Pyridaben [2-tert-butyl-5-(4-tert-butyl-benzylthio)-4-chloropyridazin-3(2H)-one], Fenpyroximate [tert-butyl(E)-4-[(1,3-dimethyl-5-phenoxypyrazol-4-yl)methyleneaminooxymethyl]benzoate], Tebfenpyrad [N-4-tert-butylbenzyl)-4-chloro-3-ethyl-1-methyl-5-pyrazol carboxamide], polynactin complexes including tetranactin, trinactin and dinactin; Milbemectin, Avermectin, Ivermectin, Azadilactin [AZAD], Pyrimidifen [5-chloro-N-[2-{4-(2-ethoxyethyl)-2,3-dimethylphenoxy}ethyl]-6-ethylpyrimidin-4-amine] and Pimetrozine [2,3,4,5-tetrahydro-3-oxo-4-[(pyridin-3-yl)-methyleneamino ]-6-methyl-1,2,4-triazine].

When the hydrazone compound of the present invention is used as an insecticide for agriculture, the application amount thereof is usually in the range of 0.1 to 100 g per 10 ares. In the case of emulsifiable concentrates, wettable powders and flowable concentrates, which are used after dilution with water, the application concentration thereof is usually in the range of 0.1 to 500 ppm. In the case of granules and dusts, they are applied as such without any dilution. When the hydrazone compound of the present invention is used as an insecticide for epidemic prevention, it is formulated into a dosage form such as emulsifiable concentrates, wettable powders and flowable concentrates, which are applied after dilution with water to a typical concentration of 0.1 to 500 ppm; or it is formulated into a dosage form such as oil sprays, aerosols, fumigants and poisonous baits, which are applied as such without any dilution.

The application amount and concentration depend upon various conditions such as type of formulation used, application time, place and method, kind of harmful insects and degree of damage, and they can be increased or decreased without limitation to the above range.

The present invention will be further illustrated by the following production examples, formulation examples and test examples, which are not to be construed to limit the scope thereof.

The following will describe production examples for various types of the hydrazone compounds of the present invention.

PRODUCTION EXAMPLE 1

A solution of 4-chloro-4'-trifluoromethylsulfonyloxybenzophenone-N'-ethoxycarbonylhydrazone (0.82 g) in N,N-dimethylformamide (5 ml) was stirred at room temperature, during which an oily mixture (80 mg) of sodium hydride containing 60% (w/w) sodium hydride was added to the solution. After stirring at room temperature for 15 minutes, ethoxyethylchloride (0.19 g) was added. Further, stirring was continued at room temperature for 1 hour, the reaction mixture was poured into water. The resultant mixture was extracted with ethyl acetate. The organic layer was washed with a saturated saline solution, dried over anhydrous magnesium sulfate, and concentrated. The residue was subjected to silica gel chromatography, which afforded 0.66 g of 4-chloro-4'-trifluoromethylsulfonyloxybenzophenone-N-ethoxymethy 1-N-ethoxycarbonylhydrazone (compound 4).

$n_D^{24.4}$ 1.5240

$^1$H-NMR (CDCl$_3$/TMS, 60 MHz) δ (ppm): 1.2 (t, J=7 Hz, 3H), 1.3 (t, J=7 Hz, 3H), 3.4 (q, J=7 Hz, 2H), 4.1 (q, J=7 Hz, 2H), 4.9 (s, 2H), 7.1–7.7 (m, 8H)

PRODUCTION EXAMPLE 2

A solution of 4-chloro-4'-trifluoromethylsulfonyloxybenzophenone-N'-acetylhydrazone (0.78 g) in N,N-dimethylformamide (4 ml) was stirred at room temperature, during which an oily mixture (0.08 g) of sodium hydride containing 60% (w/w) sodium hydride was added to the solution at a time. After stirring at room temperature for 15 minutes and finding no evolution of hydrogen gas, ethoxymethyl chloride (0.19 g) was added at a time. Further, stirring was continued at room temperature for 10 minutes, and the reaction mixture was poured into ice-water. The aqueous layer was extracted with ethyl acetate. Then, the organic layer was washed successively with water, diluted hydrochloric acid and a saturated aqueous solution of sodium bicarbonate, dried over anhydrous magnesium sulfate, and concentrated. The residue was subjected to silica gel chromatography, which afforded 0.30 g of 4-chloro-4'-trifluoromethylsulfonyloxybenzophenone-N-ethoxymethyl-N-acetylhydrazone (compound 1).

$n_D^{25.3}$ 1.5386

$^1$H-NMR (CDCl$_3$/TMS, 60 MHz) δ (ppm): 1.2 (t, J=7 Hz, 3H), 2.4 (s, 3H), 3.4 (q, J=7 Hz, 2H), 4.9 (s, 2H), 7.1–7.7 (m, 8H)

PRODUCTION EXAMPLE 3

A solution of 4-chloro-4'-trifluoromethylsulfonyloxybenzophenone-N'-ethoxycarbonylhydrazone (0.82 g) in N,N-dimethylformamide (5 ml) was stirred at room temperature, during which an oily mixture (80 mg) of sodium hydride containing 60% (w/w) sodium hydride was added to the solution. After stirring at room temperature for 15 minutes, chloroacetonitrile (0.15 g) was added. Further, stirring was continued at room temperature for 1 hour, and the reaction mixture was poured into water. The resultant mixture was extracted with ethyl acetate. The organic layer was washed with a saturated saline solution, dried over anhydrous magnesium sulfate, and concentrated. The residue was subjected to silica gel chromatography, which afforded 0.62 g of 4-chloro-4'-trifluoromethylsulfonyloxybenzophenone-N-cyanomethyl-N-ethoxycarbonylhydrazone (compound 12).

$n_D^{22.3}$ 1.5133

$^1$H-NMR (CDCl$_3$/ TMS, 60 MHz) δ (ppm):1.3(t, J=7 Hz, 3H), 4.1(q, J=7 Hz, 2H), 4.5(s, 2H), 7.1–7.7(m, 8H)

PRODUCTION EXAMPLE 4

A solution of 4-chloro-4'-methylsulfonyloxybenzophenone-N'-ethoxycarbonylhydrazone (0.77 g) in N,N-dimethylformamide (5 ml) was stirred at room temperature, during which an oily mixture (80 mg) of sodium hydride containing 60% (w/w) sodium hydride was added to the solution. After stirring at room temperature for 15 minutes, chloroacetonitrile (0.15 g) was added. Further, stirring was continued at room temperature for 1 hour, and the reaction mixture was poured into water. The resultant mixture was extracted with ethyl acetate. The organic layer was washed with a saturated saline solution, dried over anhydrous magnesium sulfate, and concentrated. The residue was subjected to silica gel chromatography, which afforded 0.50 g of 4-chloro-4'-methyl-sulfonyloxybenzophenone-N-cyanomethyl-N-ethoxycarbonylhydrazone (compound 16).

Product form: resinous $^1$H-NMR (CDCl$_3$/ TMS, 60 MHz) δ (ppm):1.17(t, J=7 Hz, 3H), 3.17 and 3.20 (each s, 3H in total), 4.02 (q, J=7 Hz, 2H), 4.47 (s, 2H), 7.13–7.77 (m, 8H)

PRODUCTION EXAMPLE 5

A solution of 4-chloro-4'-trifluoromethylsulfonyloxybenzophenone-N-ethoxycarbonylhydrazone (0.5 g) in tetrahydrofuran (6 ml) was stirred at room temperature under a nitrogen atmosphere, during which an oily mixture (50 mg) of sodium hydride containing 60% (w/w) sodium hydride was added to the solution at a time. After stirring at room temperature for 15 minutes and finding no evolution of hydrogen gas, the mixture was cooled to −78° C., and chloro-{N-(2-ethoxycarbonylethyl)-N-isopropylamino}sulfide (0.3 g) was added dropwise over 3 minutes. The reaction mixture was warmed to room temperature over 4 hours, and then poured into ice-water. Further, a saturated saline solution was added thereto. The aqueous layer was extracted with ethyl acetate, and the extract was combined with the organic layer. The combined organic layer was dried over anhydrous magnesium sulfate, and concentrated. The residue was subjected to silica gel chromatography, which afforded 0.2 g of 4-chloro-4'-trifluoromethylsulfonyloxybenzo- phenone-N-ethoxycarbonyl-N-{N'-(2-ethoxycarbonylethyl)-N'-isopropylaminosulfenyl }-hydrazone (compound 28).

$n_D^{22.3}$ 1.5353

$^1$H-NMR (CDCl$_3$/ TMS) δ (ppm):7.1–7.8 (8H, m), 4.0–4.4 (4H, m), 3.47 (2H, m), 3.38 ($^1$H, m), 2.67 (2H, t), 1.1–1.5 (12H, m)

PRODUCTION EXAMPLE 6

A solution of 4-chloro-4'-trifluoromethylsulfonyloxybenzophenone-N-acetylhydrazone (0.5 g) in tetrahydrofuran (6 ml) was stirred at room temperature under a nitrogen atmosphere, during which an oily mixture (50 mg) of sodium hydride containing 60% (w/w) sodium hydride was added to the solution at a time. After stirring at room temperature for 15 minutes and finding no evolution of hydrogen gas, the mixture was cooled to −78° C., and chloro-{N-(2-ethoxycarbonylethyl)-N-isopropylamino}sulfide (0.3 g) was added dropwise over 3 minutes. The reaction mixture was warmed to room temperature over 4 hours, and then poured into ice-water. Further, a saturated saline solution was added thereto. The aqueous layer was extracted with ethyl acetate, and the extract was combined with the organic layer. The combined organic layer was dried over anhydrous magnesium sulfate, and concentrated. The residue was subjected to silica gel chromatography, which afforded 0.2 g of 4-chloro-4'-trifluoromethylsulfonyloxybenzophenone -N-ac etyl -N- {N '-(2-ethoxycarbonylethyl)-N'-isopropylaminosulfenyl}hydrazone (compound 24).

$n_D^{23.7}$ 1.5368

$^1$H-NMR (CDCl$_3$/ TMS) δ (ppm):7.0–7.9 (8H, m), 4.05–4.4 (2H, m), 3.52 (2H, m), 3.33 (1H, m), 2.74 (2H, m), 1.1–1.5 (12H, m)

PRODUCTION EXAMPLE 7

A solution of 4-chloro-4'-trifluoromethylsulfonyloxy-benzophenone-N-ethoxYcarbonylhydrazone (0.5 g) in tetrahydrofuran (6 ml) was stirred at room temperature under a nitrogen atmosphere, during which an oily mixture (50 mg) of sodium hydride containing 60% (w/w) sodium hydride was added to the solution at a time. After stirring at room temperature for 15 minutes and finding no evolution of hydrogen gas, the mixture was cooled to −78° C., and trichloromethanesulfenyl chloride (0.3 g) was added dropwise over 3 minutes. The reaction mixture was warmed to room temperature over 4 hours, and then poured into ice-water. Further, a saturated saline solution was added thereto. The aqueous layer was extracted with ethyl acetate, and the extract was combined with the organic layer. The combined organic layer was dried over anhydrous magnesium sulfate, and concentrated. The residue was subjected to silica gel chromatography, which afforded 0.2 g of 4-chloro-4'-trifluoromethylsulfonyloxybenzophenone-N-ethoxycarbonyl-N-trichloromethanesulfenylhydrazone (compound 31 ).

$n_D^{23.9}$ 1.5440

$^1$H-NMR (CDCl$_3$/ TMS) δ (ppm):7.1–7.8 (8H, m), 4.2 (2H, br q), 1.3 (3H, m)

Further, other types of the hydrazone compounds of the present invention as shown in Tables 4 and 5 were actually produced and examined for physical properties.

TABLE 4

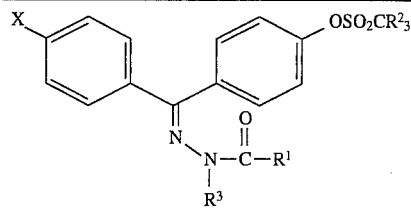

wherein R$^3$ is CH$_2$R$^4$,
and X, R$^1$, R$^2$ and R$^4$ are each as defined below.

| Compound No. | X | R$^1$ | R$^2$ | R$^4$ | Physical properties |
|---|---|---|---|---|---|
| 1 | Cl | CH$_3$ | F | OCH$_2$CH$_3$ | $n_D^{25.3}$ 1.5386 |
| 2 | Cl | CH$_3$ | F | OCH$_3$ | $n_D^{27.0}$ 1.5356 |
| 3 | Cl | CH$_3$ | F | OCH(CH$_3$)$_2$ | $n_D^{24.5}$ 1.5375 |
| 4 | Cl | OCH$_2$CH$_3$ | F | OCH$_2$CH$_3$ | $n_D^{24.4}$ 1.5240 |
| 5 | Cl | OCH$_2$CH$_3$ | F | OCH(CH$_3$)$_2$ | $n_D^{24.4}$ 1.5182 |
| 6 | Cl | CH$_2$CH$_2$CH$_3$ | F | OCH$_2$CH$_3$ | $n_D^{25.8}$ 1.5213 |
| 7 | Cl | CH$_2$CH$_3$ | F | OCH$_3$ | $n_D^{24.4}$ 1.5368 |
| 8 | Cl | CH$_2$CH$_2$CH$_3$ | F | OCH$_3$ | $n_D^{24.4}$ 1.5381 |
| 9 | Cl | CH$_2$OCH$_3$ | F | OCH$_3$ | $n_D^{24.4}$ 1.5376 |
| 10 | Cl | CH$_2$CH$_3$ | F | OCH$_2$CH$_3$ | $n_D^{19.3}$ 1.5411 |
| 11 | Cl | OCH$_3$ | F | OCH$_2$CH$_3$ | $n_D^{22.5}$ 1.5247 |
| 12 | Cl | OCH$_2$CH$_3$ | F | CN | $n_D^{22.3}$ 1.5133 |
| 13 | Cl | CH$_3$ | F | CN | $n_D^{22.3}$ 1.5473 |
| 14 | Cl | OCH$_3$ | F | CN | $n_D^{23.1}$ 1.5391 |
| 15 | Cl | CH$_2$CH$_3$ | F | CN | (resinous) |
| 16 | Cl | OCH$_2$CH$_3$ | H | CN | (resinous) |
| 17 | Br | OCH$_2$CH$_3$ | H | CN | (resinous) |
| 18 | Cl | OCH$_2$CH$_3$ | H | OCH$_2$CH$_3$ | $n_D^{24.4}$ 1.5564 |
| 19 | Br | OCH$_2$CH$_3$ | H | OCH$_2$CH$_3$ | $n_D^{24.3}$ 1.5689 |
| 20 | Br | OCH$_2$CH$_3$ | F | CN | $n_D^{27.1}$ 1.5452 |
| 21 | Br | OCH$_2$CH$_3$ | F | OCH$_2$CH$_3$ | $n_D^{24.4}$ 1.5309 |

TABLE 5

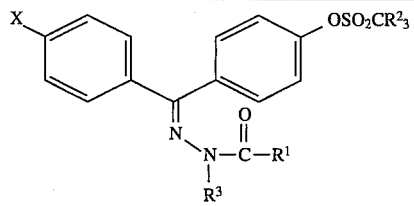

wherein $R^2$ is fluorine, $R^3$ is $SR^5$,
and X, $R^1$ and $R^5$ are each as defined below.

| Compound No. | X | $R^1$ | $R^5$ | Physical properties |
|---|---|---|---|---|
| 22 | Cl | $CH_3$ | $N(n-C_4H_9)_2$ | * |
| 23 | Cl | $CH_3$ | $N(CH_3)CO_2CH_2CH_3$ | $n_D^{22.6}$ 1.5440 |
| 24 | Cl | $CH_3$ | $N(i-C_3H_7)CH_2CH_2CO_2CH_2CH_3$ | $n_D^{23.7}$ 1.5368 |
| 25 | Cl | $CH_3$ | $N(CH_2C_6H_5)CH_2CH_2CO_2CH_2CH_3$ | $n_D^{22.5}$ 1.5643 |
| 26 | Cl | $OCH_2CH_3$ | $N(CH_2C_6H_5)CH_2CH_2CO_2CH_2CH_3$ | $n_D^{22.1}$ 1.5503 |
| 27 | Cl | $OCH_2CH_3$ | $N(CH_3)CO_2CH_2CH_3$ | $n_D^{20.0}$ 1.5345 |
| 28 | Cl | $OCH_2CH_3$ | $N(i-C_3H_7)CH_2CH_2CO_2CH_2CH_3$ | $n_D^{22.3}$ 1.5353 |
| 29 | Cl | $OCH_2CH_3$ | $N(n-C_4H_9)_2$ | $n_D^{22.3}$ 1.5269 |
| 30 | Cl | $CH_3$ | $CCl_3$ | $n_D^{23.5}$ 1.5488 |
| 31 | Cl | $OCH_2CH_3$ | $CCl_3$ | $n_D^{23.9}$ 1.5440 |
| 32 | Br | $OCH_2CH_3$ | $CCl_3$ | $n_D^{24.5}$ 1.5696 |

* NMR data of compound 22: $^1$H-NMR ($CDCl_3$/TMS) δ (ppm): 7.1–7.9 (8H, m), 3.1 (4H, br d), 2.4 (3H, s), 1.6 (4H, m), 1.3 (4H, m), 0.95 (6H, m)

The following will describe several formulation examples for the hydrazone compounds of the present invention. In these formulation examples, the active ingredients are designated by the corresponding compound numbers as shown in Tables 4 and 5, and "parts" are by weight unless otherwise stated.

FORMULATION EXAMPLE 1

Emulsifiable concentrates

First, 10 parts of each of the compounds 1 to 32 are separately dissolved in 35 parts of xylene and 35 parts of dimethylfonnmnide. Each of these mixtures is mixed with 14 pans of polyoxyethylene styrylphenyl ether and 6 parts of calcium dodecylbenzenesulfonate, and the resultant mixture is well stirred to give a 10% emulsifiable concentrate of each compound.

FORMULATION EXAMPLE 2

Wettable Powders

First, 20 parts of each of the compounds 1 to 32 are separately added to a mixture of 4 parts of sodium lauryl sulfate, 2 parts of calcium lignin sulfonate, 20 parts of synthetic hydrated silicon hydroxide fine powder and 54 parts of diatomaceous earth, and the resultant mixture is stirred with a mixer to give a 20% wettable powder of each compound.

FORMULATION EXAMPLE 3

Granules

To 5 parts of each of the compounds 1 to 32 are added 5 parts of sodium dodecylbenzenesulfonate, 30 parts of bentonite and 60 parts of clay, and the resultant mixture is well stirred. Then, a suitable amount of water is added to each of these mixtures, which was further stirred, granulated with a granulator, and then air-dried to give a 5% granule of each compound.

FORMULATION EXAMPLE 4

Dusts

First, 1 part of each of the compounds 1 to 32 dissolved separately in a suitable amount of acetone is mixed with 5 parts of synthetic hydrated silicon hydroxide fine powder, 0.3 parts of PAP and 93.7 parts of clay. Then, the resultant mixture was stirred with a mixer, and acetone is evaporated to give a 1% dust of each compound.

FORMULATION EXAMPLE 5

Flowables

First, 10 parts of each of the compounds 1 to 32 are separately added to an aqueous solution containing 6 parts of polyvinyl alcohol, and the resultant mixture is stirred with a mixer to give a dispersing agent. To this dispersing agent are added 40 parts of an aqueous solution containing 0.05 parts of xanthan gum and 0.1 parts of aluminum magnesium silicate, followed by further addition of 10 pans of propylene glycol, and the resultant mixture is mixed by gentle stirring to give a 10% water-based emulsion of each compound.

FORMULATION EXAMPLE 6

Oil Solutions

First, 0.1 parts of each of the compounds 1 to 32 are separately dissolved in 5 parts of xylene and 5 parts of trichloroethane. The resultant solution is mixed with 89.9 parts of deodorized kerosine to give a 0.1% oil solution of each compound.

FORMULATION EXAMPLE 7

Oil-based Aerosols

First, 0.1 parts of each of the compounds 1 to 32, 0.2 parts of tetramethrin, 0.1 parts of d-phenothrin and 10 parts of trichloroethane are dissolved in 59.6 parts of deodorized kerosine, and an aerosol vessel is filled with the resultant solution. Then, the vessel is equipped with a valve, through which 30 parts of a propellant (liquefied petroleum gas) are charged under pressure to give an oil-based aerosol of each compound.

FORMULATION EXAMPLE 8

Water-Based Aerosols

An aerosol vessel is filled with 50 parts of pure water and a mixture of 0.2 parts of each of the compounds 1 to 32, 0.2 parts of d-allethrin, 0.2 parts of d-phenothrin, 5 parts of xylene, 3.4 parts of deodorized kerosine and 1 part of an emulsifier [ATMOS 300 (registered trade mark of Atlas Chemical Co.)]. Then, the vessel is equipped with a valve, through which 40 parts of a propellant (liquefied petroleum gas) are charged under pressure to give a water-based aerosol of each compound.

The following test examples will illustrate that the hydrazone compounds of the present invention are useful as an active ingredient of insecticides. In these test examples, the hydrazone compounds of the present invention are designated by the corresponding numbers as shown in Tables 4 and 5, and the compounds used for comparison are designated by the corresponding symbols as defined below.

Compound A: 4-chloro-4'-(trifluoromethylsulfonyloxy)benzophenone-N'-acetylhydrazone (which is included in the compounds of the general formula described in the U.S. Pat. No. 4,344,893)

Compound B: 4-chloro-4'-(trifluoromethylsulphonyloxy)benzophenone-N'-(ethoxycarbonyl)hydrazone (which is identical to compound 83 as described in column 20 of the U.S. Pat. No. 4,344,893)

TEST EXAMPLE 1

Insecticidal Test on *Spodoptera Litura*

Each of the test compounds was formulated into an emulsifiable concentrate according to Formulation Example 1, which was then diluted with water to a concentration of 500 ppm. With 2 ml of the dilution was impregnated 13 g of an artificial diet for *Spodoptera litura* prepared in a polyethylene cup having a diameter of 11 cm. Then, ten fourth-instar larvae of *Spodoptera litura* were set free in the cup. After six days, the survival of larvae was examined to determine the mortality.

As a result, it was found that the compounds 1 to 32 exhibited the mortality of at least 80%. By contrast, the mortality in the non-treated field was 0%.

TEST EXAMPLE 2

Ovicidal and Larvicidal Tests on *Plutella Xylostella*

Each of the test compounds was formulated into an emulsifiable concentrate according to Formulation Example 1, which was then diluted with water to a concentration of 50 ppm. In the dilution were dipped four sprouted Japanese radishes which have been harvested five to six days after the seeding (i.e., two Japanese radishes on which 100 to 150 eggs of *Plutella xyiostella* were laid and two Japanese radishes on which no egg was laid), followed by air drying, and they were put in a polyethylene cup having a diameter of 5.5 cm. After six days, the hatching and the survival of larvae were examined to determine the ovicidal and larvicidal rates.

As a result, it was found that the compounds 1–8, 10–15, 18–25 and 30–32 exhibit the ovicidal and larvicidal rate of at least 90%. By contrast, the ovicidal and larvicidal rate in the non-treated field was less than 90%.

TEST EXAMPLE 3

Insecticidal Test on Larvae of *Diabrotica Undecirnpunctata*

Each of the test compounds was formulated into an emulsifiable concentrate according to Formulation Example 1, which was then diluted with water to a concentration of 50 ppm. On the bottom of a polyethylene cup having a diameter of 5.5 cm was laid a filter paper having the same diameter. Then, 1 ml of the dilution was dropped on the filter paper. Then, about 30 eggs of *Diabrotica undecimpunctata* were put on the filter paper, and a sprouted corn as a diet was put in the cup. After eight days, the survival of hatched larvae was examined.

As a result, it was found that the compounds 1–7, 9–12, 14–22, 24–25 and 30–32 exhibited the mortality of at least 90%. By the contrast, the mortality in the non-treated field was less than 90%.

TEST EXAMPLE 4

Insecticidal Test on Larvae of *Blattella Germanica*

Each of the test compounds was formulated into an emulsifiable concentrate according to Formulation Example 1, which was then diluted with water to a concentration of 500 ppm. On the bottom of a polyethylene cup having a diameter of 5.5 cm was laid a filter paper having the same diameter. Then, 0.7 ml of the dilution was dropped on the filter paper, and about 30 mg of sugar as a bait was uniformly put on the filter paper. Ten male adults of *Blattella germanica* were set free in the cup, and a lid was put on the cup. After six days, the survival of male adults was examined to determine the mortality.

As a result, it was found that the compounds 1–3, 5, 7–9, 12–14, 20–23, 25–28 and 30 exhibited the mortality of 100%.

TEST EXAMPLE 5

Insecticidal Test on *Culex Pipiens Pallens*

Each of the test compounds was formulated into an emulsifiable concentrate according to Formulation Example 1, which was then diluted with water (active ingredient concentration, 3.5 ppm). To 100 ml of deionized water was added 0.7 ml of the dilution, in which twenty final instar larvae of *Culex pipiens pallens* were set free. After one day, the survival of the larvae was examined to determine the mortality.

As a result, it was found that the compounds 1–32 exhibited the mortality of at least 90%.

TEST EXAMPLE 6

Acute Toxicity by Oral Application to Mice

Each of the test compounds, i.e., compound 1, 4, 12, 24 and 28 of the present invention and compounds A and B for comparison, was diluted to a predetermined concentration with corn oil. After about twenty-hour fasting, 0.1 ml of the dilution per 10 g weight for each ICR male 6-week old mouse (weight, 24 to 31 g) was forcibly applied to the stomach of each animal. The mice was given food and water since four hours after the application, and kept in a cage. Seven days after the application, the survival of the mice was examined to determine the mortality (4 mice per group). The results are shown in Table 6.

TABLE 6

| Test compound | Dosage (mg/kg) | Mortality (%) |
|---|---|---|
| 1 | 30 | 0 |
| 4 | 100 | 0 |
| 12 | 30 | 0 |
| 24 | 30 | 0 |
| 28 | 100 | 0 |
| A | 30 | 100 |
| B | 30 | 40 |

What is claimed is:

1. A hydrazone compound of the general formula (I):

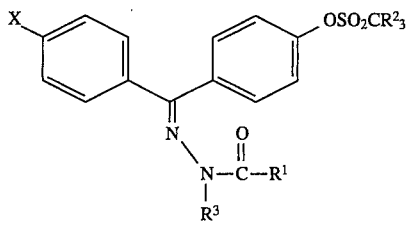 (I)

wherein X is halogen;

$R^1$ is hydrogen; $C_1$–$C_4$ alkyl which may be optionally substituted with halogen, cyano or $C_1$–$C_4$ alkoxy; or $C_1$–$C_4$ alkoxy which may be optionally substituted with halogen;

$R^2$'s are the same or different and are independently hydrogen or fluorine; $R^3$ is a group of the general formula (II):

 (II)

wherein $R^4$ is cyano or $C_1$–$C_4$ alkoxy;

or $R^3$ is a group of the general formula (III):

 (III)

wherein $R^5$ is $C_1$–$C_6$ alkyl which may be optionally substituted with halogen; phenyl which may be optionally substituted with halogen, nitro or $C_1$–$C_{10}$ alkyl which may be optionally substituted with halogen; a group of the general formula (IV):

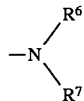 (IV)

wherein $R^6$ and $R^7$ are the same or different and are independently $C_1$–$C_6$ alkyl which may be optionally substituted with halogen, cyano or $C_1$–$C_6$ alkoxy; $C_3$–$C_{16}$ alkenyl which may be optionally substituted with halogen; $C_3$–$C_{16}$ alkynyl which may be optionally substituted with halogen; phenyl which may be optionally substituted with halogen or $C_1$–$C_{10}$ alkyl which may be optionally substituted with halogen; $C_7$–$C_{16}$ phenylalkyl which may be optionally substituted with halogen or $C_1$–$C_{10}$ alkyl which may be optionally be substituted with halogen; $C_2$–$C_{16}$ alkoxycarbonyl; or $C_3$–$C_{16}$ alkoxycarbonylalkyl.

2. A compound according to claim 1, wherein X is chlorine; $R^1$ is $C_1$–$C_4$ alkyl or $C_1$–$C_4$ alkoxy; $R^2$'s are all fluorine; $R^4$ is cyano, methoxy or ethoxy; and $R^5$ is trichloromethyl or a group of the general formula (IV) wherein $R^6$ and $R^7$ are the same or different and are independently $C_1$–$C_4$ alkyl; benzyl which may be optionally substituted with halogen or $C_1$–$C_4$ alkyl which may be optionally substituted with halogen; $C_2$–$C_3$ alkoxycarbonyl; or $C_3$–$C_5$ alkoxycarbonylalkyl.

3. A compound according to claim 2, wherein $R^1$ is $C_1$–$C_4$ alkoxy; $R^4$ is cyano; and $R^5$ is a group of the general formula (IV) wherein $R^6$ and $R^7$ are the same or different and are independently $C_1$–$C_4$ alkyl, benzyl, $C_2$–$C_3$ alkoxycarbonyl or $C_3$–$C_5$ alkoxycarbonylalkyl.

4. A compound according to claim 3, wherein $R^1$ is methoxy or ethoxy.

5. Compound of claim 1 being 4-Chloro-4'-trifluoromethylsulfonyloxybenzophenone-N-cyanomethyl-N-ethoxycarbonylhydrazone.

6. Compound of claim 1 being 4-Chloro-4'-trifluoromethylsulfonyloxybenzophenone-N-cyanomethyl-N-methoxycarbonylhydrazone.

7. Compound of claim 1 being 4-Chloro-4'-trifluoromethylsulfonyloxybenzophenone-N-ethoxycarbonyl-N-{N'-(2-ethoxycarbonylethyl)-N'-benzylaminosulfenyl}hydrazone.

8. Compound of claim 1 being 4-Chloro-4'-trifluoromethylsulfonyloxybenzophenone-N-ethoxycarbonyl-N-(N'-ethoxycarbonyl-N'-methylaminosulfenyl)hydrazone.

9. Compound of claim 1 being 4-Chloro-4'-trifluoromethylsulfonyloxybenzophenone-N-ethoxycarbonyl-N-{N'-(2-ethoxycarbonylethyl)-N'-isopropylaminosulfenyl}hydrazone.

10. Compound of claim 1 being 4-Chloro-4'-trifluoromethylsulfonyloxybenzophenone-N-ethoxycarbonyl-N-{N', N'-dibutylaminosulphenyl)hydrazone.

11. Compound of claim 1 being 4-Chloro-4'-trifluoromethylsulfonyloxybenzophenone-N-ethoxycarbonyl-N-trichloromethylsulfenylhydrazone.

12. An insecticide comprising a hydrazone compound of claim 1 as an active ingredient.

13. A method for controlling harmful insects, comprising applying an effective amount of a hydrazone compound of claim 1.

* * * * *